(12) United States Patent
Dai et al.

(10) Patent No.: US 11,427,583 B2
(45) Date of Patent: Aug. 30, 2022

(54) COMPOUND, OLED DISPLAY PANEL AND DISPLAY DEVICE

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wenpeng Dai, Shanghai (CN); Wei Gao, Shanghai (CN); Lei Zhang, Shanghai (CN); Jinghua Niu, Shanghai (CN); Ying Liu, Shanghai (CN); Ping An, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

(*) Notice: Subject to any disclaimer, the term of this patent is extended or adjusted under 35 U.S.C. 154(b) by 446 days.

(21) Appl. No.: 16/591,755

(22) Filed: Oct. 3, 2019

(65) Prior Publication Data

US 2020/0407359 A1 Dec. 31, 2020

(30) Foreign Application Priority Data

Jun. 28, 2019 (CN) .......................... 201910579361.9

(51) Int. Cl.
*C07D 209/82* (2006.01)
*C07D 221/06* (2006.01)
(Continued)

(52) U.S. Cl.
CPC ......... *C07D 471/06* (2013.01); *C07D 405/14* (2013.01); *C07D 409/14* (2013.01);
(Continued)

(58) Field of Classification Search
CPC .. C07D 471/06; C07D 405/14; C07D 409/14; C07D 7/0814; H01L 51/0052;
(Continued)

(56) References Cited

FOREIGN PATENT DOCUMENTS

| CN | 1535089 A | 10/2004 |
|---|---|---|
| CN | 103319695 A | 9/2013 |

(Continued)

OTHER PUBLICATIONS

Yi Han et al; "Synthesis, Characterization, and Properties of Diazapyrenes via Bischier—Napieralski Reaction"; J. Org. Chem. 2019, 84, 3953-3959.

*Primary Examiner* — Vu A Nguyen
(74) *Attorney, Agent, or Firm* — Kilpatrick Townsend & Stockton LLP

(57) ABSTRACT

The present disclosure relates to the field of organic electroluminescence materials and particularly relates to a compound, an OLED display panel and a display device. The compound according to the present disclosure has a structure represented by a formula (I) or a formula (II):

formula (I)

(Continued)

(a)

(b)

-continued

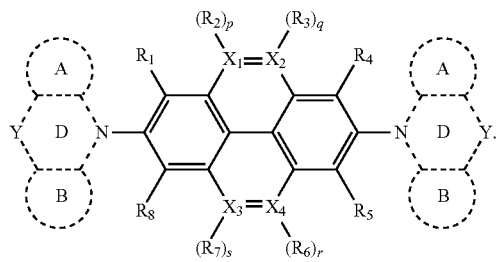

formula (II)

20 Claims, 1 Drawing Sheet

(51) Int. Cl.
*C07D 221/18* (2006.01)
*C07D 241/38* (2006.01)
*C07D 265/34* (2006.01)
*C07D 279/14* (2006.01)
*H01L 51/00* (2006.01)
*H01L 51/50* (2006.01)
*C07D 471/06* (2006.01)
*C07D 405/14* (2006.01)
*C07D 409/14* (2006.01)
*C07F 7/08* (2006.01)

(52) U.S. Cl.
CPC ........ *C07F 7/0814* (2013.01); *H01L 51/0052* (2013.01); *H01L 51/0059* (2013.01); *H01L 51/0067* (2013.01); *H01L 51/0072* (2013.01); *H01L 51/0094* (2013.01); *H01L 51/5012* (2013.01)

(58) Field of Classification Search
CPC ............. H01L 51/0059; H01L 51/0067; H01L 51/0072; H01L 51/0094; H01L 51/5012
See application file for complete search history.

(56) References Cited

FOREIGN PATENT DOCUMENTS

| | | | |
|---|---|---|---|
| CN | 103347883 A | 10/2013 | |
| CN | 107226793 A | 10/2017 | |
| CN | 108682299 A | 10/2019 | |
| WO | 2010006890 A1 | 1/2010 | |

COMPOUND, OLED DISPLAY PANEL AND DISPLAY DEVICE

CROSS-REFERENCE TO RELATED APPLICATION

This application claims priority of Chinese Patent Application No. 201910579361.9, filed on Jun. 28, 2019, which is hereby incorporated by reference in its entirety.

FIELD

The present disclosure relates to the field of organic electroluminescence materials and particularly relates to a compound, an OLED display panel and a display device.

BACKGROUND

As a new-generation display technology, an organic electroluminescence material (OLED) has the advantages of ultra-thinness, self-luminescence, wide view angle, fast response, high luminous efficiency, good temperature adaptability, simple production process, low driving voltage, low energy consumption and the like and has been extensively applied to the industries of panel display, flexible display, solid-state illumination, vehicular display, etc.

OLED can be divided into two kinds, i.e., electrofluorescence and electrophosphorescence according to luminescence mechanisms, fluorescence results from radiation damping transition of singlet excitons, and phosphorescence means light emitted from radiation damping to a ground state of triplet excitons. A ratio of formation probability of the singlet excitons to the triplet excitons is 1:3 according to a self-spin quantum statistical theory. The internal quantum efficiency of a fluorescent material does not exceed the limitation of 25%, and the external quantum efficiency of the fluorescent material is generally lower than 5%; and the internal quantum efficiency of an electrophosphorescence material theoretically reaches 100%, and the external quantum efficiency of the electrophosphorescence material can reach 20%. In 1998, Prof. Ma, Yuguang of Jilin University in our country and Prof. Forrest of Princeton University in US separately reported that an osmium complex and a platinum complex are doped into a luminescent layer as dyes, an electrophosphorescence phenomenon is successfully obtained and explained for the first time, and the prepared phosphorescence material is applied to electroluminescence devices.

At present, among three kinds of base-color materials, i.e., red, green and blue materials for preparing panchromatic organic light-emitting diodes, red light materials and green light materials already basically meet requirements on industrialization, while blue light materials still have a relatively big distance from industrialized application in the embodiments of fluorescence efficiency, color purity, lifetime, brightness and the like, which becomes an issue in the present industry. At present, the blue light materials mainly take carbazole, anthracene, pyrene, perylene, fluorene, styrene and the like as core structures. The seeking of a new blue light material core structure and further designing of a novel blue light emitting material have an important significance in improving the performance of a blue light OLED.

SUMMARY

The present disclosure provides a compound, an OLED display panel and a display device.

According to one embodiment of the present disclosure, a compound is provided and has a structure represented by a formula (I) or a formula (II):

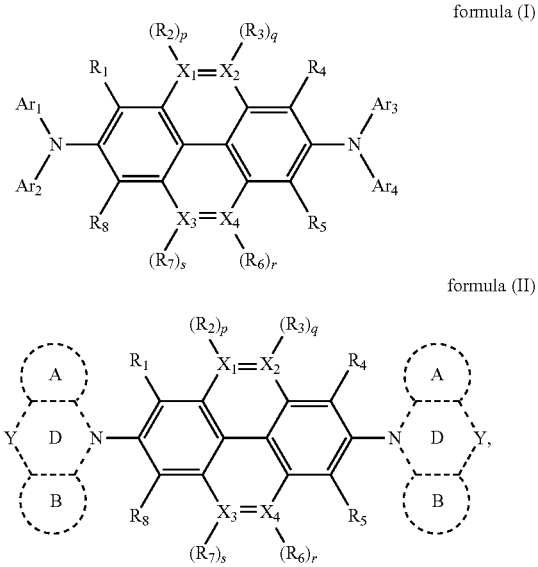

in the formula (I) and the formula (II), $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl; p, q, r and s each are independently selected from 0 or 1;

in the formula (I), $Ar_1$-$Ar_4$ each are independently selected from at least one of substituted or unsubstituted aryl with the number of carbon atoms to be C6-C30, substituted or unsubstituted heterocyclyl with the number of carbon atoms to be C5-C20, alkylsilicyl with the number of carbon atoms to be C3-C30, or arylsilicyl with the number of carbon atoms to be C8-C30; and in the formula (II), Y is selected from a S atom, an O atom, a N atom or a C atom; A and B each are independently selected from at least one of substituted or unsubstituted C6-C40 aryl, substituted or unsubstituted C4-C40 heteroaryl, and D is selected from a N-atom-containing five-membered ring or six-membered ring.

According to one embodiment of the present disclosure, in $X_1$-$X_4$, $X_1$ and $X_2$ are N atoms, and $X_3$ and $X_4$ are C atoms.

According to one embodiment of the present disclosure, in $X_1$-$X_4$, $X_1$ and $X_3$ are N atoms, and $X_2$ and $X_4$ are C atoms.

According to one embodiment of the present disclosure, in $X_1$-$X_4$, $X_1$ and $X_4$ are N atoms, and $X_2$ and $X_3$ are C atoms.

According to one embodiment of the present disclosure, $R_3$ and $R_7$ are the same, and $R_2$ and $R_6$ are the same.

According to one embodiment of the present disclosure, $R_1$ and $R_5$ are the same, and $R_4$ and $R_8$ are the same.

According to one embodiment of the present disclosure, $Ar_1$ and $Ar_4$ are the same, and $Ar_2$ and $Ar_3$ are the same.

According to one embodiment of the present disclosure, $R_1$-$R_8$ each are independently selected from C1-C20 alkyl and C3-C20 cycloalkyl.

According to one embodiment of the present disclosure, at least two of p, q, r and s are selected from 0.

According to one embodiment of the present disclosure, in $R_1$-$R_8$, the aryl with the number of carbon atoms to be C6-C30 is selected from one or more of phenyl, biphenyl, 9,9-fluorenyl, terphenyl, naphthyl, anthryl, phenanthryl, 9,10-benzophenanthryl, 1,2-benzophenanthryl, acenaphthylenyl, perylenyl, pyrenyl and indenyl; and the heterocyclyl with the number of carbon atoms to be C5-C20 is selected from one or more of furyl, thienyl, pyrryl, oxazolyl, thiazolyl, pyrazolyl, pyranyl, imidazolyl, pyridyl, pyrazinyl, pyrimidyl, 1,3,4-oxadiazolyl, 1,2,4-triazolyl, 1,3,5-triazinyl, indolyl, benzimidazolyl, dibenzofuryl, dibenzothienyl, carbazolyl, quinolyl, quinoxalyl, ortho-phenanthrolinyl, phenazinyl and pyridazinyl.

According to one embodiment of the present disclosure, the alkylsilicyl with the number of carbon atoms to be C3-C30 is selected from trimethyl silicyl, triethyl silicyl, and the arylsilicyl with the number of carbon atoms to be C8-C30 is selected from phenyl trimethyl silicyl, phenyl triethyl silicyl.

According to one embodiment of the present disclosure, in $R_1$-$R_8$, the aryl with the number of carbon atoms to be C6-C30 is selected from at least one of phenyl, naphthyl, biphenyl, 9,9-fluorenyl and terphenyl; and the heterocyclyl with the number of carbon atoms to be C5-C20 is selected from at least one of dibenzofuryl, dibenzothienyl and pyridyl.

According to one embodiment of the present disclosure, the compound has a structure represented by a formula (II-1)

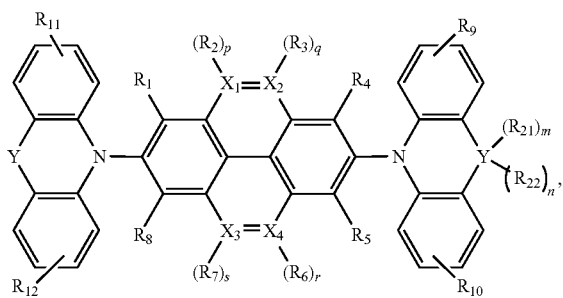

formula (II-1)

and, $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl; p, q, r, s, m and n each are independently selected from 0 or 1; and Y is selected from a S atom, an O atom, a N atom or a C atom; $R_9$, $R_{10}$, $R_{11}$ and $R_{12}$ each are independently selected from at least one of a hydrogen atom, C1-C6 alkyl, C1-C6 alkoxy, —$CF_3$, —S—$CH_3$ and —CN—; and $R_{21}$ and $R_{22}$ each are independently selected from at least one of a hydrogen atom, C1-C6 alkyl and C1-C6 alkoxy.

According to one embodiment of the present disclosure, Y is selected from a S atom.

According to one embodiment of the present disclosure, the compound has a structure represented by a formula (II-2)

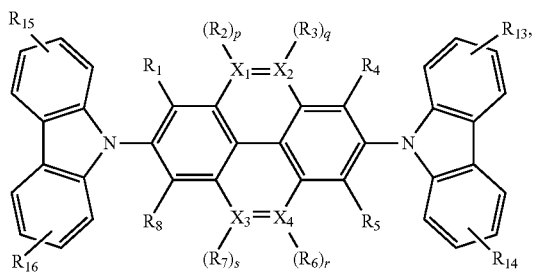

formula (II-2)

and, $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl;

p, q, r and s each are independently selected from 0 or 1; and $R_{13}$, $R_{14}$, $R_{15}$ and $R_{16}$ each are independently selected from at least one of a hydrogen atom, C1-C6 alkyl, C1-C6 alkoxy, —$CF_3$, —S—$CH_3$ and —CN—.

According to one embodiment of the present disclosure, the compound is any one selected from

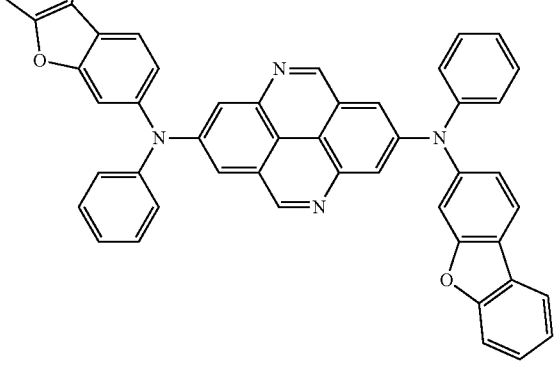

P1

P2
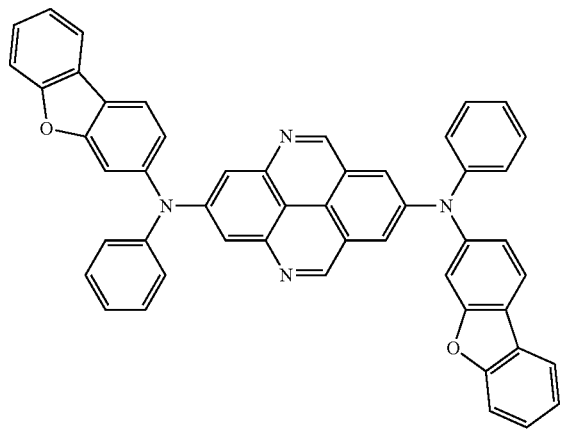
P3
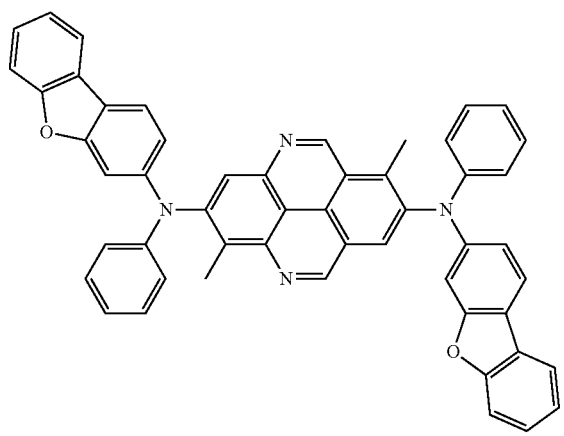
P4
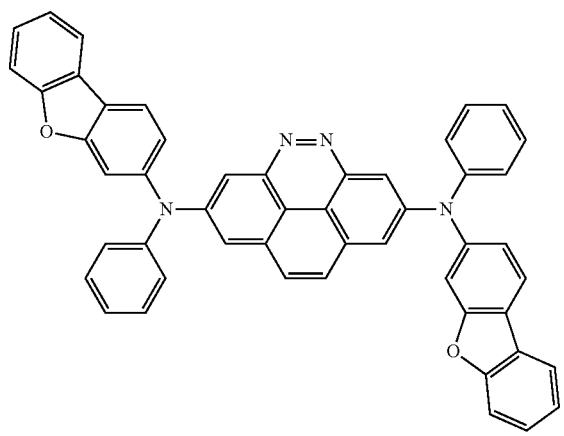
P5
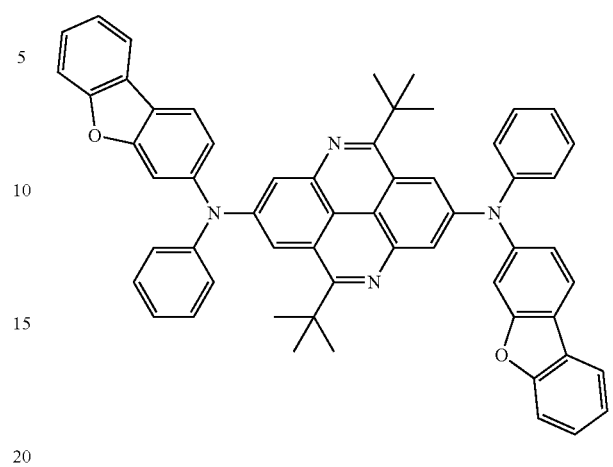
P6
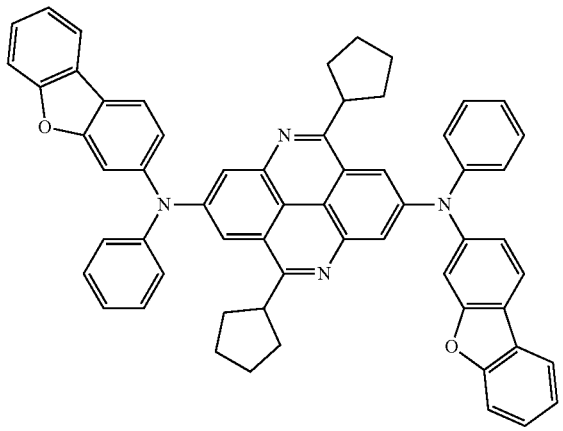
P7
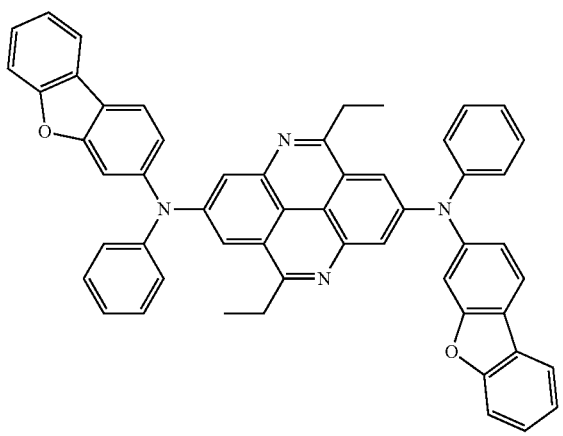

P8
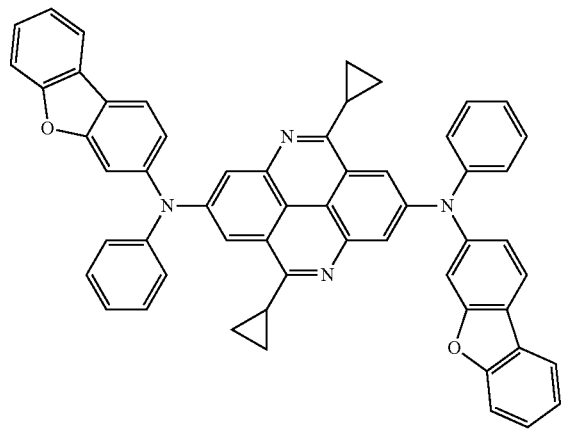
P9
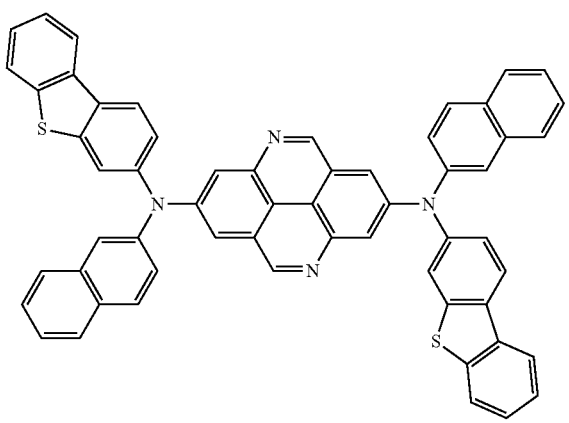
P10
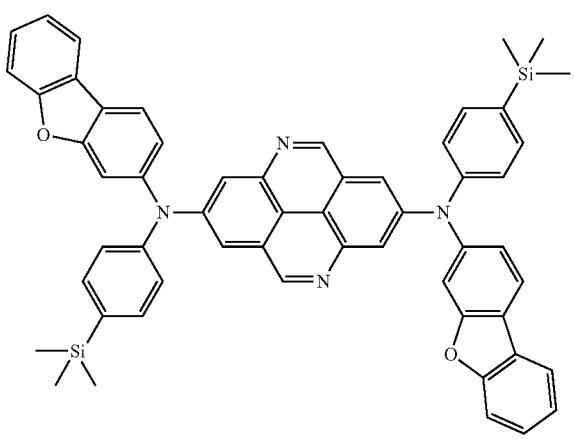
P11
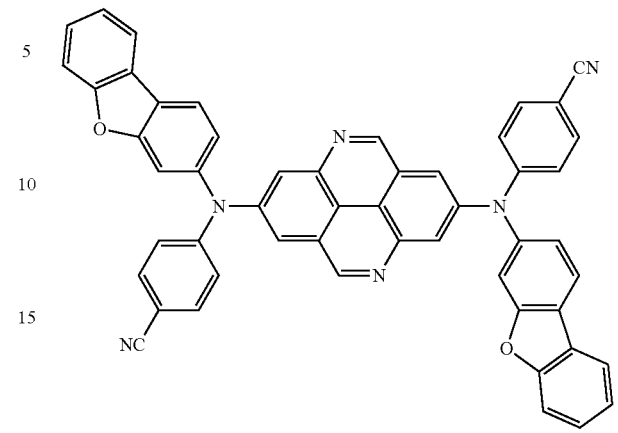
P12
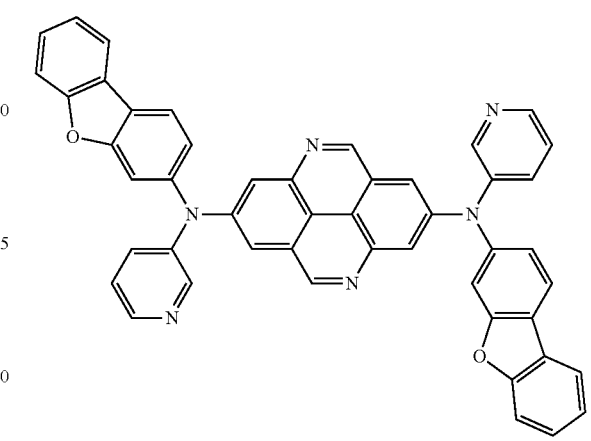
P13
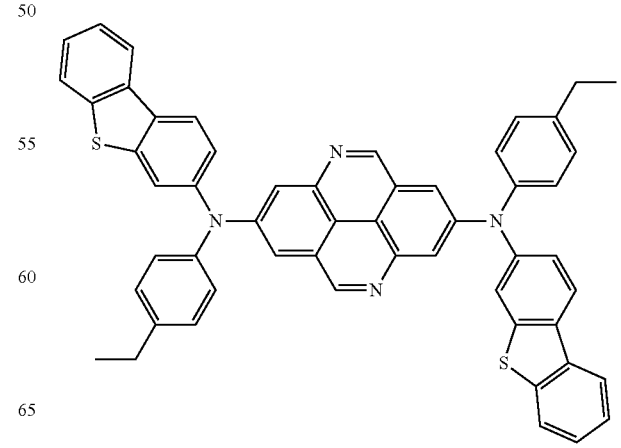

P14
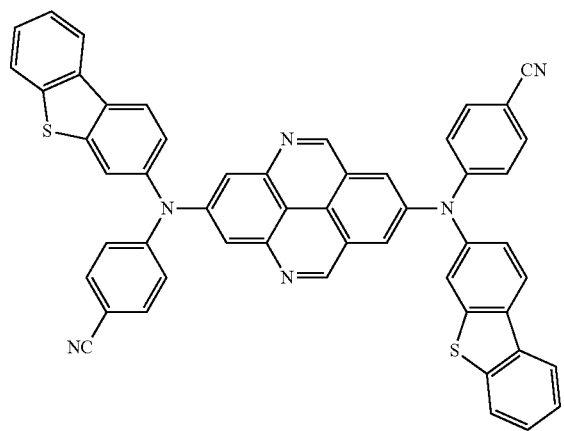
P17
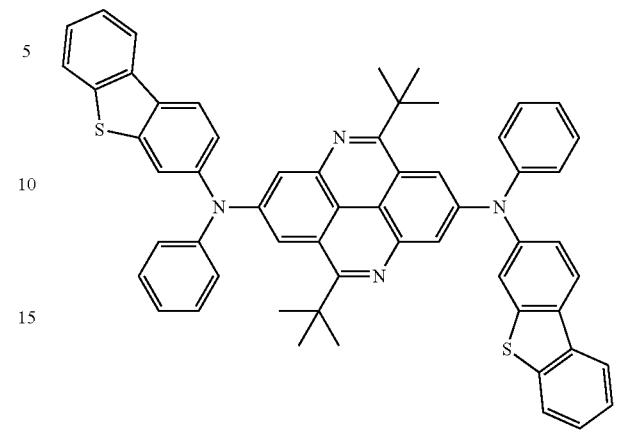
P15
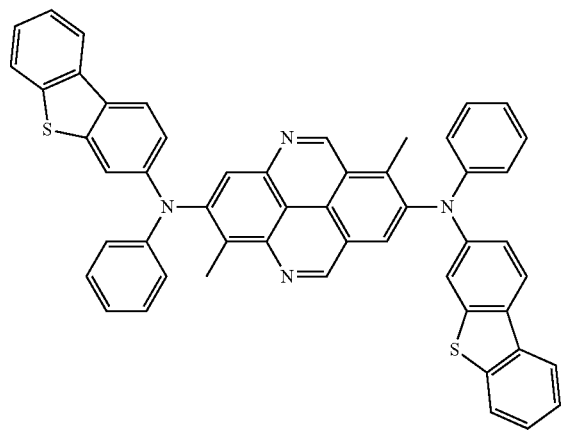
P18
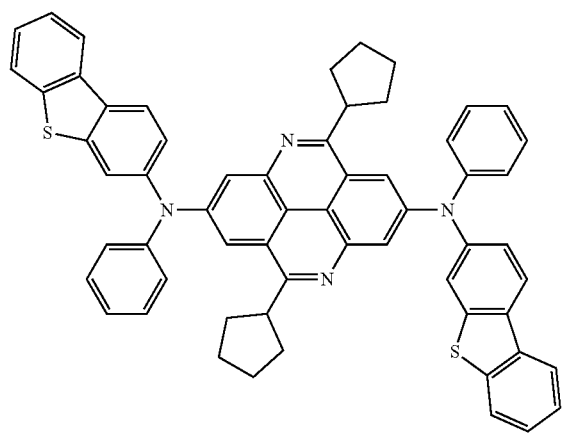
P16
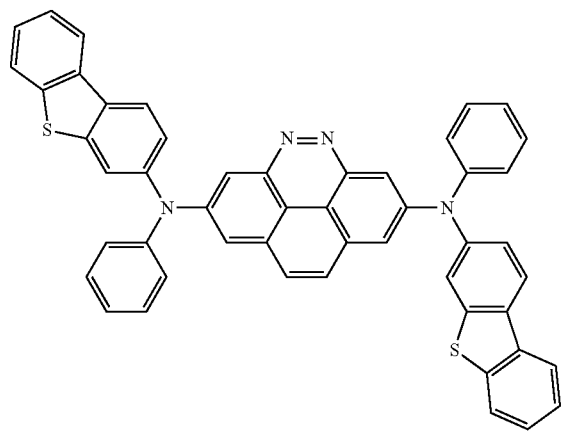
P19
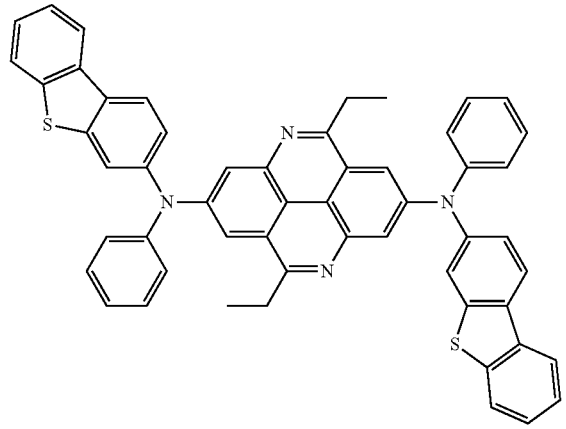

P20
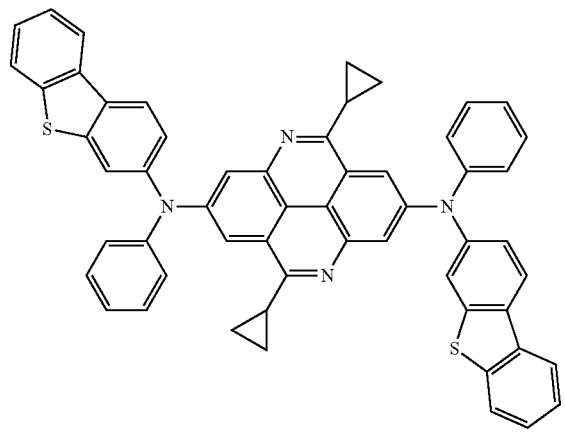
P23
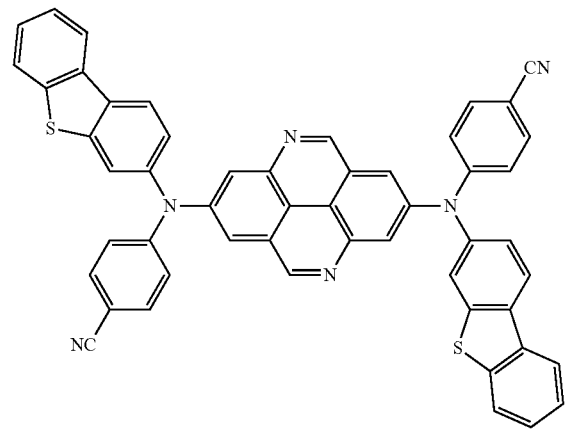
P21
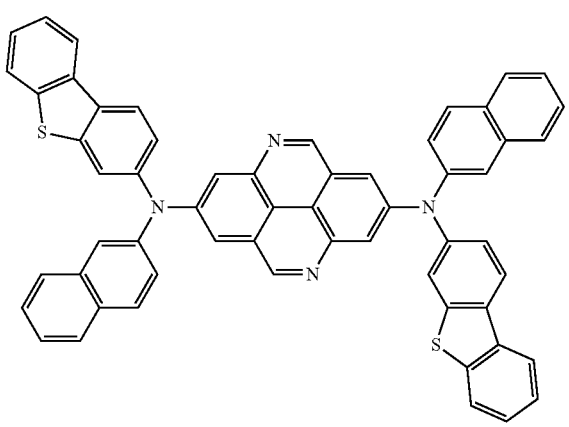
P24
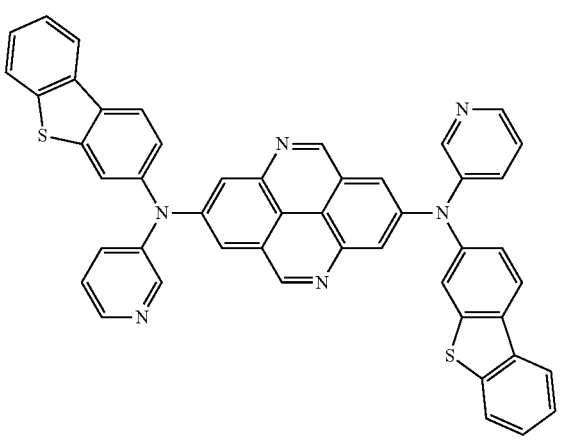
P25
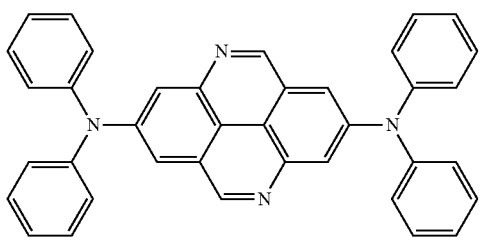
P22
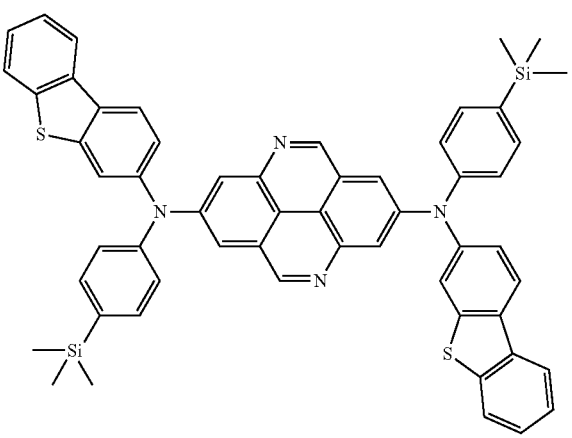
P26
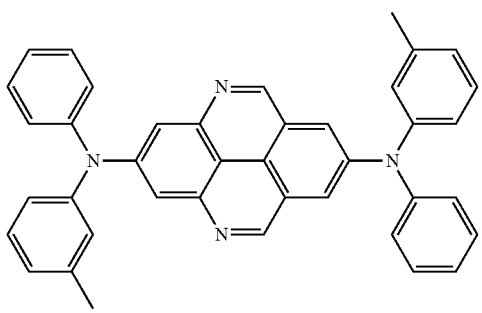

P27
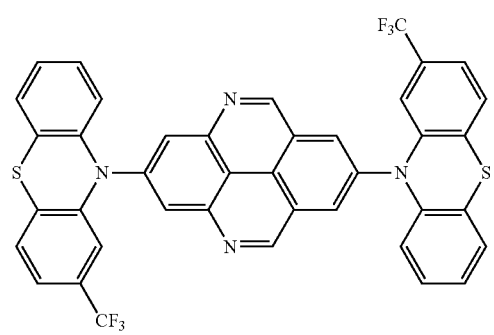
P28
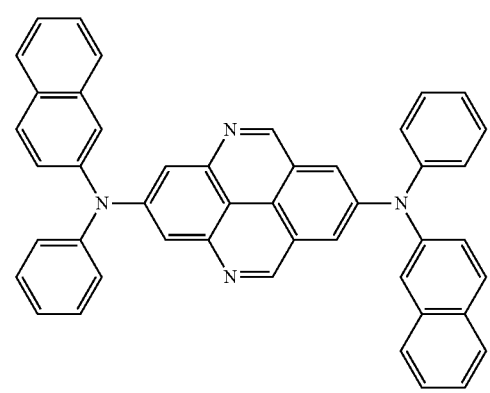
P29
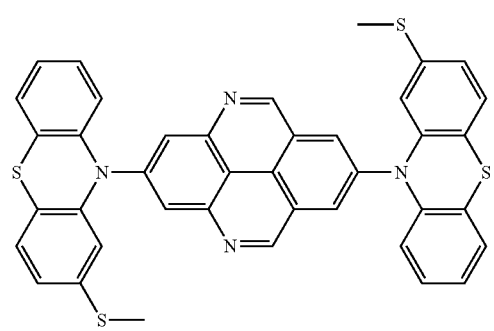
P30
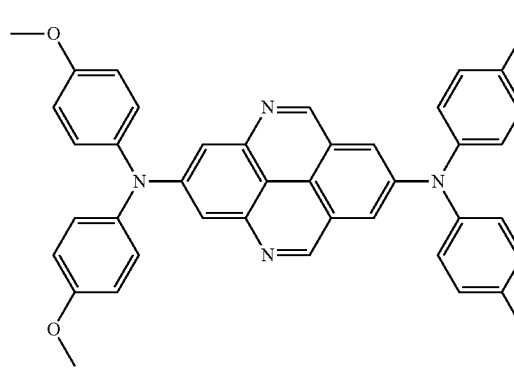
P31
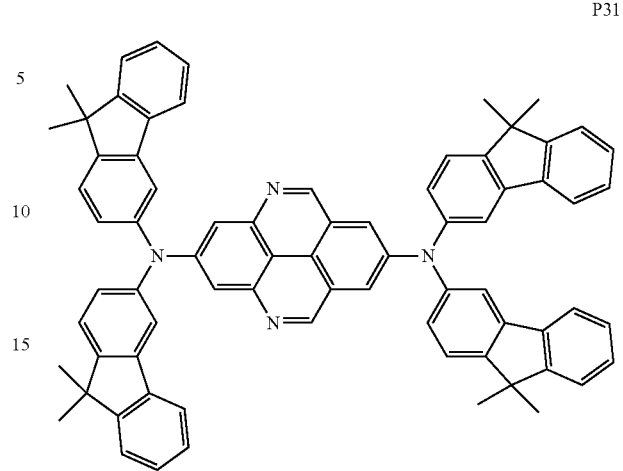
P32
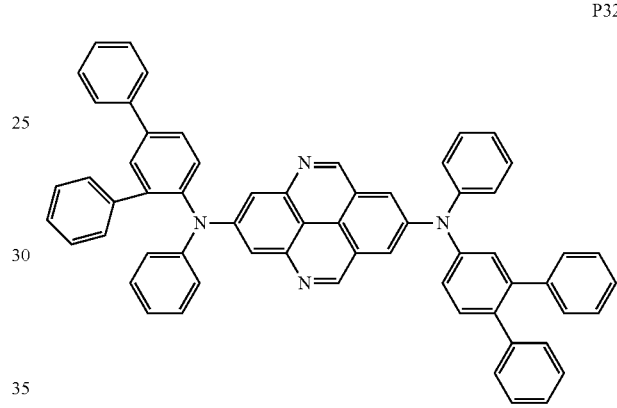
P33
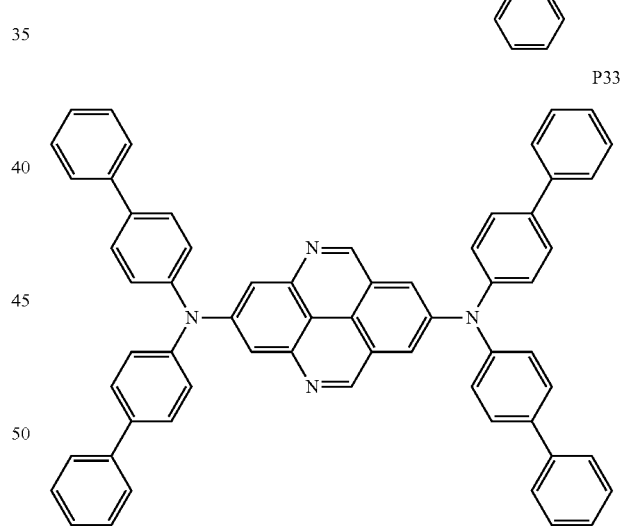
P34
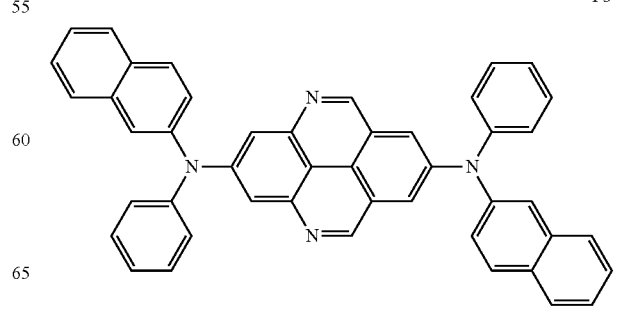

P35
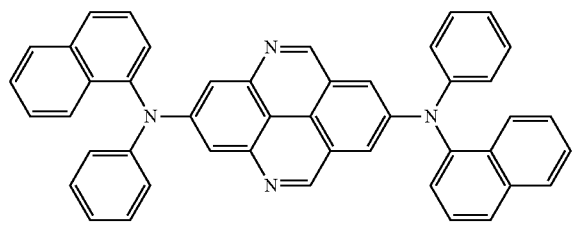
P36
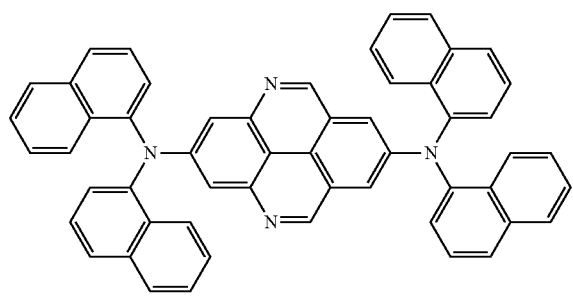
P37
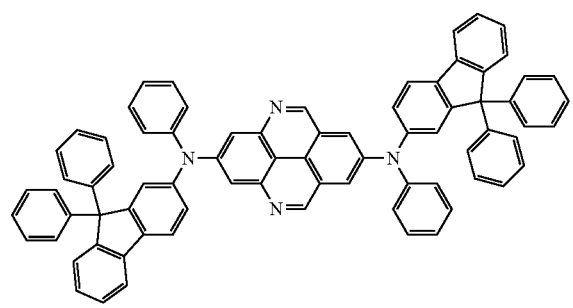
P38
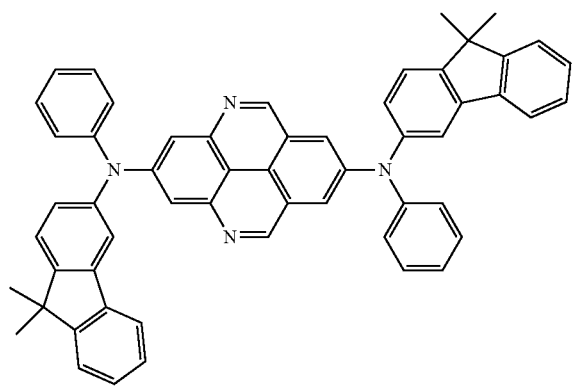
P39
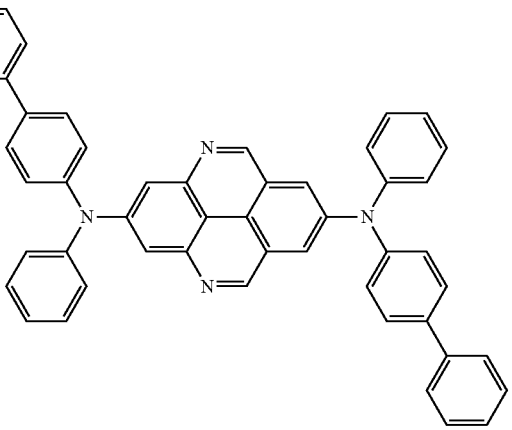
P40
P41
P42
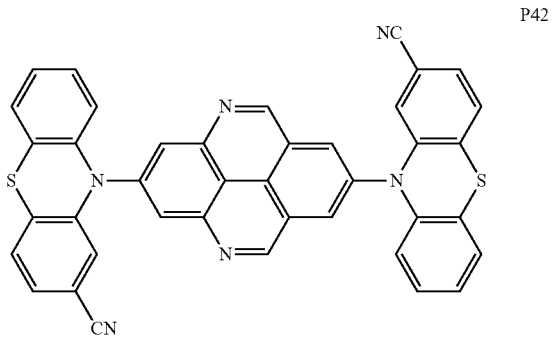

P43
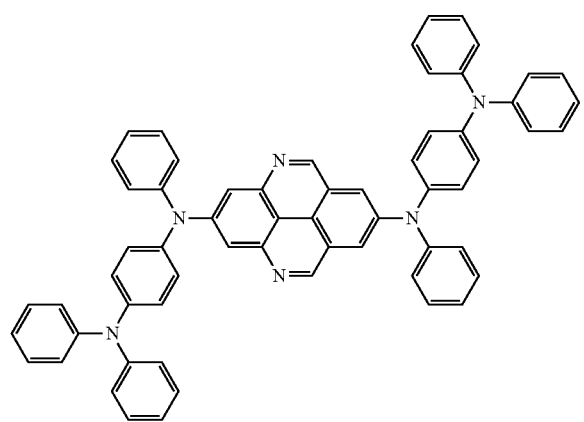
P44
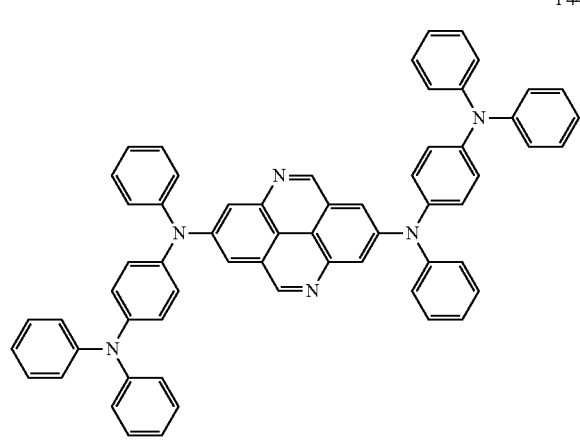
P45
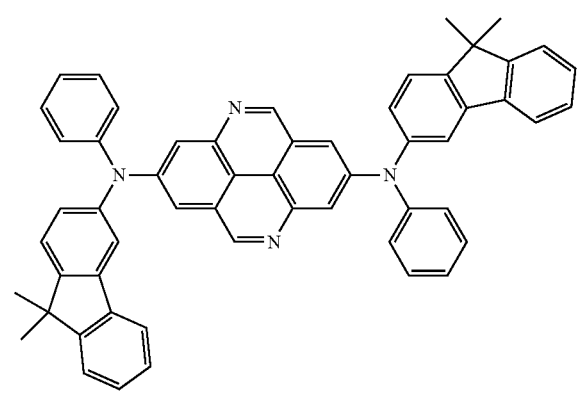
P46
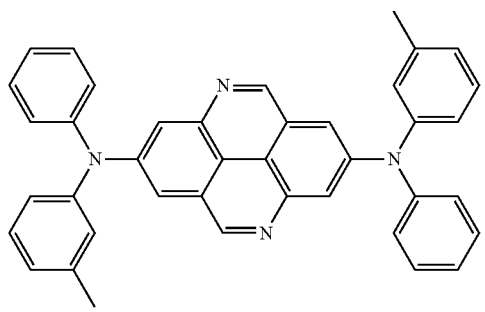
P47
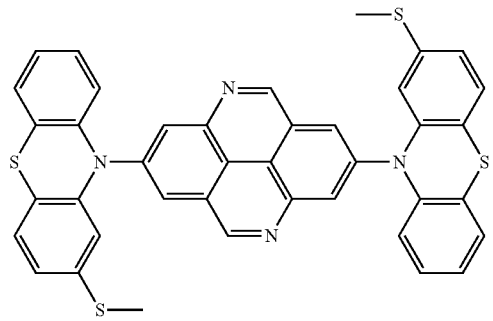
P48
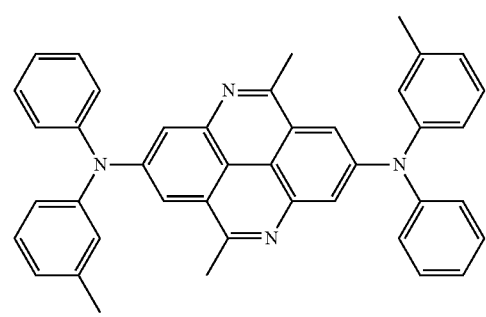
P49
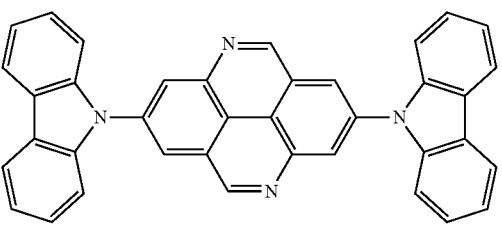
P50
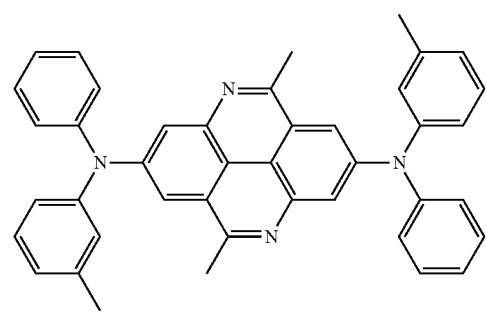
P51
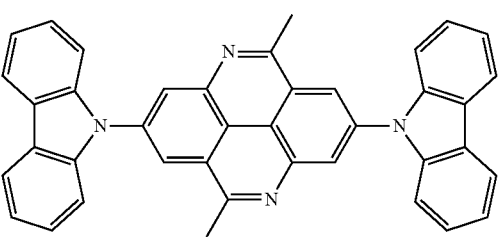

According to one embodiment of the present disclosure, the compound is any one selected from
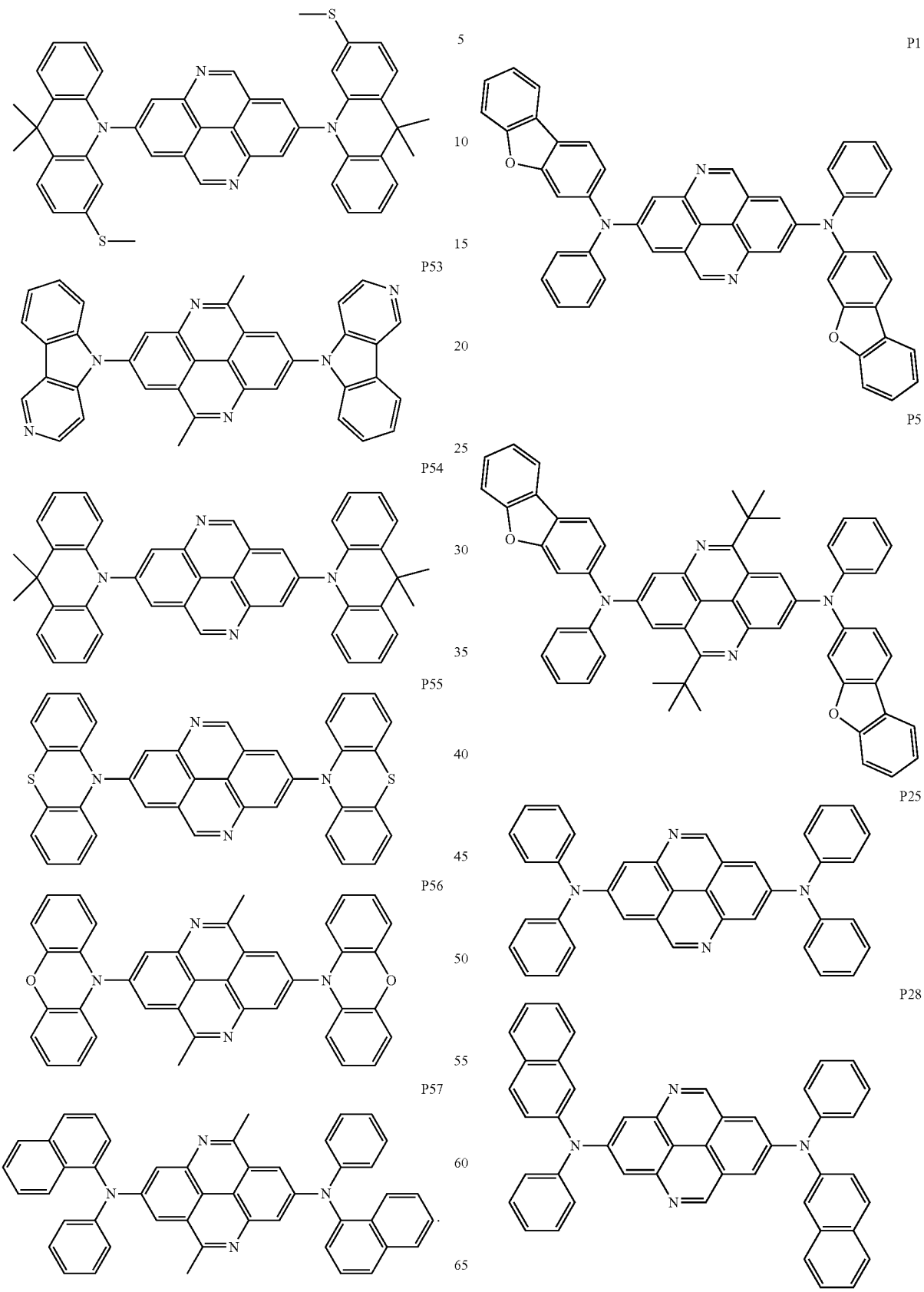

-continued

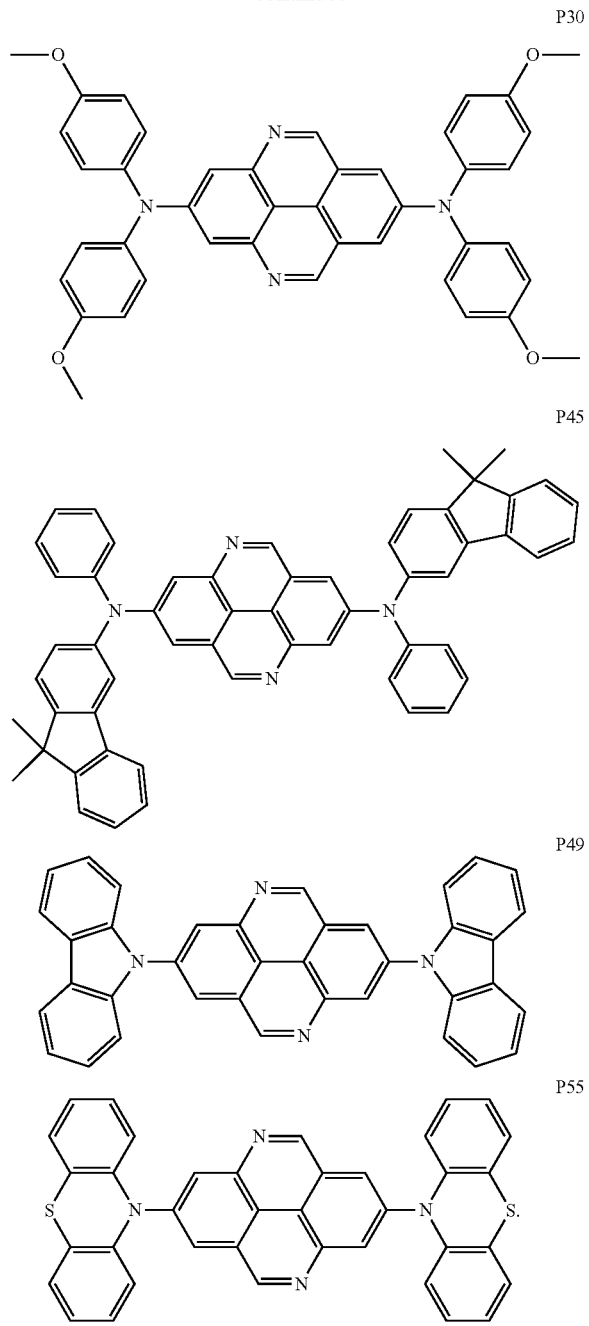

According to another embodiment of the present disclosure, an OLED display panel is provided and comprises a first electrode, a second electrode and an organic film layer arranged between the first electrode and the second electrode;

the organic film layer comprises a luminescent layer; and a luminescent material of the luminescent layer comprises the compounds provided by the present disclosure.

According to one embodiment of the present disclosure, the luminescent material serves as a host material or a guest material of the luminescent layer, or the luminescent material independently forms the luminescent layer to prepare a non-doped OLED display panel.

According to one embodiment of the present disclosure, the luminescent material is a blue light material.

According to another embodiment of the present disclosure, a display device is provided and comprises the OLED display panel according to the present disclosure.

The display device according to the present disclosure, for example, may be a mobile phone display screen, a computer display screen, a liquid crystal television display screen, etc.

As a blue light material, the energy difference between the highest occupied molecular orbital (HOMO) and the lowest unoccupied molecular orbital (LUMO) must be large enough to emit high-energy blue light. An aromatic system with a big conjugate ring has better oxidation-reduction stability, however, it easily generates minor HOMO-LUMO energy difference, and meanwhile, it also easily generates a triplet excited state with low energy.

In the present disclosure, by introducing a nitrogen atom into a mother core structure and connecting a conjugate ring system by adopting a non-carbon group, powerful conjugation interaction can be lowered, so that the degree of delocalization of the HOMO and the LUMO is inhibited, the energy level difference of HOMO-LUMO can be bigger, and meanwhile, a $T_1$ energy level is relatively high, and can emit high-quality blue, sky-blue and navy-blue light.

In an aza-containing pyrene structure of the present disclosure, conjugation is broken off by the nitrogen atom, a molecular excited state can be improved, and thus, the brightness is improved; and an arylamine three-dimensional structure can improve a thermal effect caused by molecular aggregation and accumulation, so that the lifetime is prolonged.

The compound provided by the present disclosure has proper HOMO and LUMO values, a hole transport layer and an electron transport layer can be better matched, and thus, the gathering of holes and electrons on the luminescent layer and balancing of transporting of a current carrier are facilitated; and meanwhile, the compound has higher singlet and triplet energy levels and excellent thermal stability and film stability, so that the increase of luminous efficiency is facilitated.

A blue light emitting material is prepared from the aza aromatic compounds provided by the present disclosure as a new core structure of the fluorescent material, the organic compounds of this category are lower in driving voltage, higher in luminous efficiency and longer in service life, and the wavelength of emitted light can be finely adjusted through positions of substituents and heteroatoms, so that the organic compounds can be applied to electroluminescence devices.

Figure 1:
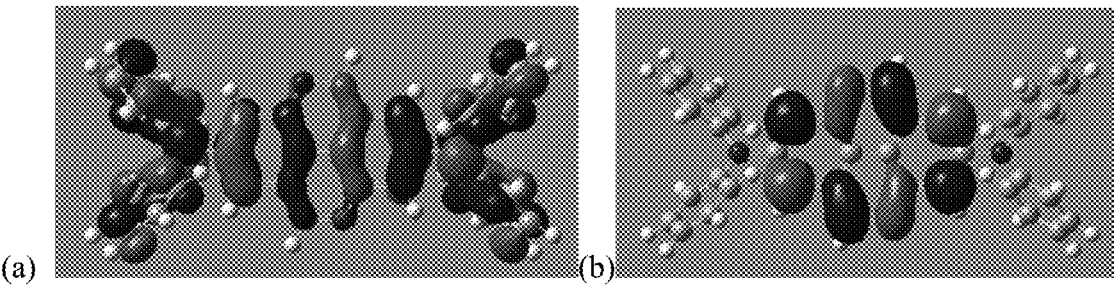
FIG. 1 is HOMO and LUMO energy level distribution diagrams of a compound P1; and, (a) in FIG. 1 is a HOMO energy level distribution diagram of the compound P1, and (b) in FIG. 1 is a LUMO energy level distribution diagram of the compound P1.

In one embodiment, 1—substrate, 2—first electrode, 3—organic film layer, 4—second electrode, and 5—display screen.

DETAILED DESCRIPTION OF THE EMBODIMENTS

Specific embodiments are only intended to describe the present disclosure, rather than limit contents of the present disclosure, and the present disclosure will be further described and represented below with reference to the specific embodiments.

The present disclosure provides a compound, an OLED display panel and a display device.

According to one embodiment of the present disclosure, a compound is provided and has a structure represented by a formula (I) or a formula (II):

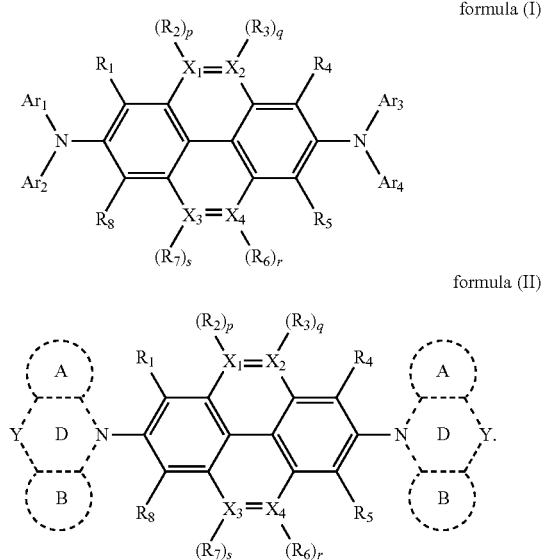

formula (I)

formula (II)

In the formula (I) and the formula (II), $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl;

p, q, r and s each are independently selected from 0 or 1;

in the formula (I), $Ar_1$-$Ar_4$ each are independently selected from at least one of substituted or unsubstituted aryl with the number of carbon atoms to be C6-C30, substituted or unsubstituted heterocyclyl with the number of carbon atoms to be C5-C20, alkylsilicyl with the number of carbon atoms to be C3-C30, or arylsilicyl with the number of carbon atoms to be C8-C30; and in the formula (II), Y is selected from a S atom, an O atom, a N atom or a C atom; A and B each are independently selected from at least one of substituted or unsubstituted C6-C40 aryl, substituted or unsubstituted C4-C40 heteroaryl, and D is selected from a N-atom-containing five-membered ring or six-membered ring.

In the present disclosure, by introducing a nitrogen atom into a mother core structure and connecting a conjugate ring system by adopting a non-carbon group, powerful conjugation interaction can be lowered, so that the degree of delocalization of the HOMO and the LUMO is inhibited, the energy level difference of HOMO-LUMO can be bigger, and meanwhile, a $T_1$ energy level is relatively high, and can emit high-quality blue, sky-blue and navy-blue light.

In an aza-containing pyrene structure of the present disclosure, conjugation is broken off by the nitrogen atom, a molecular excited state can be improved, and thus, the brightness is improved; and an arylamine three-dimensional structure can improve a thermal effect caused by molecular aggregation and accumulation, so that the lifetime is prolonged.

The compound provided by the present disclosure has proper HOMO and LUMO values, a hole transport layer and an electron transport layer can be better matched, and thus, the gathering of holes and electrons on the luminescent layer and balancing of transporting of a current carrier are facilitated; and meanwhile, the compound has higher singlet and triplet energy levels and excellent thermal stability and film stability, so that the increase of luminous efficiency is facilitated.

A blue light emitting material is prepared from the aza aromatic compounds provided by the present disclosure as a new core structure of the fluorescent material, the organic compounds of this category are lower in driving voltage, higher in luminous efficiency and longer in service life, and the wavelength of emitted light can be finely adjusted through positions of substituents and heteroatoms, so that the organic compounds can be applied to electroluminescence devices.

According to one embodiment of the present disclosure, in $X_1$-$X_4$, $X_1$ and $X_2$ are N atoms, and $X_3$ and $X_4$ are C atoms.

According to one embodiment of the present disclosure, in $X_1$-$X_4$, $X_1$ and $X_3$ are N atoms, and $X_2$ and $X_4$ are C atoms.

According to one embodiment of the present disclosure, in $X_1$-$X_4$, $X_1$ and $X_4$ are N atoms, and $X_2$ and $X_3$ are C atoms.

According to one embodiment of the present disclosure, $R_3$ and $R_7$ are the same, and $R_2$ and $R_6$ are the same.

According to one embodiment of the present disclosure, $R_1$ and $R_5$ are the same, and $R_4$ and $R_8$ are the same.

According to one embodiment of the present disclosure, $Ar_1$ and $Ar_4$ are the same, and $Ar_2$ and $Ar_3$ are the same.

According to one embodiment of the present disclosure, $R_1$-$R_8$ each are independently selected from C1-C20 alkyl and C3-C20 cycloalkyl.

According to one embodiment of the present disclosure, at least two of p, q, r and s are selected from 0.

According to one embodiment of the present disclosure, in $R_1$-$R_8$, the aryl with the number of carbon atoms to be C6-C30 is selected from one or more of phenyl, biphenyl, 9,9-fluorenyl, terphenyl, naphthyl, anthryl, phenanthryl, 9,10-benzophenanthryl, 1,2-benzophenanthryl, acenaphthylenyl, perylenyl, pyrenyl and indenyl; and the heterocyclyl with the number of carbon atoms to be C5-C20 is selected from one or more of furyl, thienyl, pyrryl, oxazolyl, thiazolyl, pyrazolyl, pyranyl, imidazolyl, pyridyl, pyrazinyl, pyrimidyl, 1,3,4-oxadiazolyl, 1,2,4-triazolyl, 1,3,5-triazinyl, indolyl, benzimidazolyl, dibenzofuryl, dibenzothienyl, carbazolyl, quinolyl, quinoxalyl, ortho-phenanthrolinyl, phenazinyl and pyridazinyl.

According to one embodiment of the present disclosure, the alkylsilicyl with the number of carbon atoms to be C3-C30 is selected from trimethyl silicyl, triethyl silicyl, and the arylsilicyl with the number of carbon atoms to be C8-C30 is selected from phenyl trimethyl silicyl, phenyl triethyl silicyl.

According to one embodiment of the present disclosure, in $R_1$-$R_8$, the aryl with the number of carbon atoms to be C6-C30 is selected from at least one of phenyl, naphthyl, biphenyl, 9,9-fluorenyl and terphenyl; and the heterocyclyl with the number of carbon atoms to be C5-C20 is selected from at least one of dibenzofuryl, dibenzothienyl and pyridyl.

According to one embodiment of the present disclosure, the compound has a structure represented by a formula (II-1)

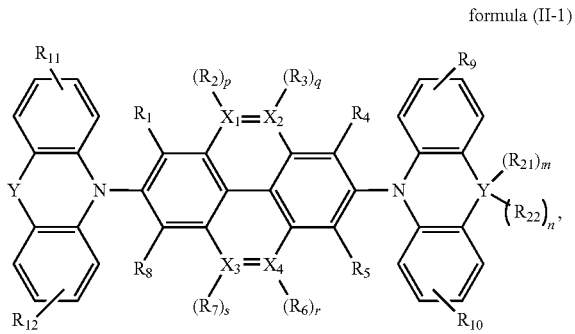

formula (II-1)

and, $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl;

p, q, r, s, m and n each are independently selected from 0 or 1; and

Y is selected from a S atom, an O atom, a N atom or a C atom; $R_9$, $R_{10}$, $R_{11}$ and $R_{12}$ each are independently selected from at least one of a hydrogen atom, C1-C6 alkyl, C1-C6 alkoxy, —$CF_3$, —S—$CH_3$ and —CN—; and $R_{21}$ and $R_{22}$ each are independently selected from at least one of a hydrogen atom, C1-C6 alkyl and C1-C6 alkoxy.

According to one embodiment of the present disclosure, Y is selected from a S atom.

According to one embodiment of the present disclosure, the compound has a structure represented by a formula (II-2)

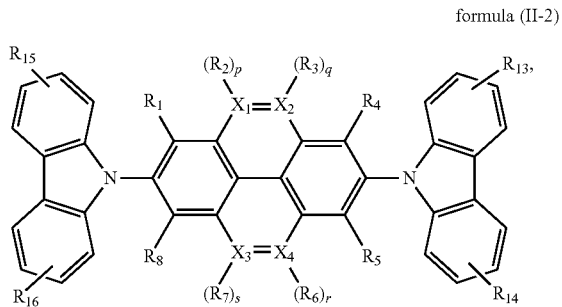

formula (II-2)

and, $X_1$-$X_4$ each are independently selected from a C atom or a N atom, and at least two of $X_1$-$X_4$ are N atoms; and $R_1$-$R_8$ each are independently selected from at least one of a hydrogen atom, substituted or unsubstituted C1-C20 alkyl, substituted or unsubstituted C3-C20 cycloalkyl, substituted or unsubstituted C3-C20 heterocyclyl, substituted or unsubstituted C6-C40 aryl, substituted or unsubstituted C4-C40 heteroaryl, substituted or unsubstituted C10-C60 condensed aryl, or substituted or unsubstituted C10-C60 condensed heteroaryl;

p, q, r and s each are independently selected from 0 or 1; and $R_{13}$, $R_{14}$, $R_{15}$ and $R_{16}$ each are independently selected from at least one of a hydrogen atom, C1-C6 alkyl, C1-C6 alkoxy, —$CF_3$, —S—$CH_3$ and —CN—.

According to one embodiment of the present disclosure, the compound is any one selected from P1 to P55.

According to one embodiment of the present disclosure, the compound is any one selected from P1, P5, P25, P28, P30, P45, P49 and P55.

According to another embodiment of the present disclosure, an OLED display panel is provided and comprises a first electrode, a second electrode and an organic film layer arranged between the first electrode and the second electrode;

the organic film layer comprises a luminescent layer; and a luminescent material of the luminescent layer comprises the compounds provided by the present disclosure.

According to one embodiment of the present disclosure, the luminescent material serves as a host material or a guest material of the luminescent layer, or the luminescent material independently forms the luminescent layer to prepare a non-doped OLED display panel.

According to one embodiment of the present disclosure, the luminescent material is a blue light material.

According to one embodiment of the present disclosure, the luminescent material serves as dopant material of the luminescent layer. When the luminescent material serves as the dopant material of the luminescent layer, the host material preferably comprises one or more selected from materials such as 2,8-bis(diphenylphosphinyl)dibenzothiophene (PPT), 4,4'-di(9-carbazolyl)biphenyl (CBP), 2,8-bis(diphenylphosphine oxide)dibenzofuran (PPF), bis(4-(9H-carbazol-9-yl)phenyl)diphenylsilane (SiCz), bis[2-(diphenylphosphino)phenyl]ether oxide (DPEPO), 1,3-bis[3,5-di(pyridin-3-yl)phenyl]benzene (BMPYPHB), 4,6-bis(3,5-di(3-pyridin)ylphenyl)-2-methylpyrimidine (B3PYMPM), 9-(3-(9H-carbazol-9-yl)phenyl)-9H-carbazol-3-cyano (mCPCN), 9-phenyl-9-[4-(triphenyl silyl)phenyl]-9H-fluorene (TPSi-F), polyvinyl carbazole (PVK) and polyfluorene (PFO), but not only limited to the above several host materials.

The luminescent material of the present disclosure can also serve as a host material of the luminescent layer. When the luminescent material serves as the host material of the luminescent layer, the dopant material is selected from fluorescent materials such as BczVBi, coumarin-6 and DCJTB, etc., the dopant material can also be selected from phosphorescence materials and can also be selected from TADF dopant luminescent materials, but not limited to the above several materials.

The organic film layer according to the present disclosure further comprises a hole injection layer (HIL), a hole transport layer (HTL), an electron barrier layer (EBL), a hole barrier layer (HBL), an electron transport layer (ETL) and an electron injection layer (EIL).

Hole injection materials, hole transport materials and electron barrier materials may be selected from materials such as N,N'-diphenyl-N,N'-(1-naphthyl)-1,1'-biphenyl-4,4'-diamine (α-NPD), 4,4',4"-tri(carbazol-9-yl)triphenylamine (TCTA), 1,3-dicarbazol-9-ylbenzene (mCP), 4,4'-di(9-carbazolyl)biphenyl (CBP), 3,3'-di(N-carbazolyl)-1,1'-biphenyl (mCBP), 2,3,6,7,10,11-hexacyano-1,4,5,8,9,12-hexaazatriphenylene (HATCN), 4,4'-cyclohexylidenebis[N,N-bis(4- methylphenyl)aniline] (TAPC), N,N'-diphenyl-N,N'-(1-naphthyl)-1,1'-biphenyl-4,4'-diamine (α-NPB), N,N'-bis(naphthalen-2-yl)-N,N'-di(phenyl)biphenyl-4,4'-diamine (NPB), poly(3,4-ethylenedioxythiophene)-polystyrene sulfonate (PEDOT:PSS), polyvinyl carbazole (PVK), 9-phenyl-3,9-dicarbazole (CCP) and molybdenum trioxide ($MoO_3$), etc., but not limited to the above several materials.

Hole barrier materials, electron transport materials and electron injection materials may be selected from materials such as 2,8-bis(diphenylphosphinyl)dibenzothiophene (PPT), TSPO1, TPBi, 2,8-bis(diphenylphosphine oxide)dibenzofuran (PPF), bis[2-(diphenylphosphino)phenyl]ether oxide (DPEPO), lithium fluoride (LiF), 4,6-bis(3,5-di(3-pyridin)ylphenyl)-2-methylpyrimidine (B3PYMPM), 4,7-diphenyl-1,10-phenanthroline (Bphen), 1,3,5-tri[(3-pyridyl)-3-phenyl]benzene (TmPyBP), tri[2,4,6-trimethyl-3-(3-pyridyl)phenyl]borane (3TPYMB), 1,3-bis(3,5-dipyridin-3-ylphenyl)benzene (B3PYPB), 1,3-bis[3,5-di(pyridin-3-yl)phenyl]benzene (BMPYPHB), 2,4,6-tri(biphen-3-yl)-1,3,5-triazine (T2T), diphenylbis[4-(pyridin-3-yl)phenyl]silane (DPPS), caesium carbonate (Cs2O3), bis(2-methyl-8-quinolinolato-N1,O8)-(1,1'-biphenyl-4-olato)aluminum (BAlq), 8-hydroxyquinoline-lithium (Liq) and tri(8-hydroxyquinoline)aluminum ($Alq_3$), etc., but not limited to the above several materials.

According to the present disclosure, the anode material may be metal, for example copper, gold, silver, ferrum, chromium, nickel, manganese, palladium, platinum, etc.; the anode material may be metal oxide, for example, metal oxides such as indium oxide, zinc oxide, indium-tin oxide (ITO), indium-zinc oxide (IZO), etc.; the anode material may be alloy; and the anode material may be an electric-conductive polymer, for example polyaniline, polypyrrole, poly(3-methylthiophene), etc. Besides the above-mentioned materials conducive to hole injection and combinations thereof, the anode material may also be other known materials suitable for serving as an anode.

According to the present disclosure, the cathode material may be metal, for example aluminum, magnesium, silver, indium, tin, titanium, etc.; the cathode material may be alloy, for example Mg/Ag; the cathode material may be a composite material of metal and inorganic compounds, for example multilayer metallic materials, such as LiF/Al, $LiO_2$/Al, $BaF_2$/Al, etc. Besides the above-mentioned materials conducive to electron injection and combinations thereof, the cathode material may also be other known materials suitable for serving as a cathode.

According to the present disclosure, the substrate may be a rigid substrate (borosilicate glass, float soda-lime glass, glass with high refractive index, stainless steel, etc.) and may also be a flexible substrate (for example, a polyimide (PI) plastic substrate, a polyethylene terephthalate (PET) plastic substrate, a polyethylene naphthalate (PEN) plastic substrate, a polyethersulfone resin substrate (PES), a polycarbonate (PC) plastic substrate, an ultra-thin flexible glass substrate, a metal foil substrate, etc.).

Figure 2:
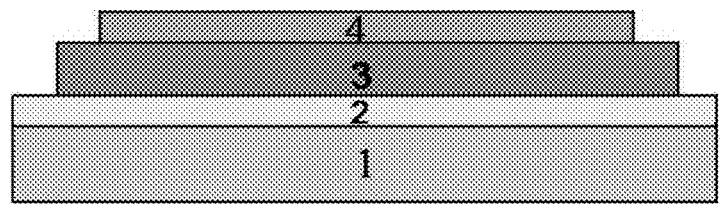
FIG. 2 is a structural schematic diagram of an OLED display panel of the present disclosure.

A structure of the OLED display panel according to the present disclosure is shown in FIG. 2, a substrate 1 is made of glass or other suitable materials (for example plastics); a first electrode 2 is a transparent electrode of ITO, IGZO or the like; an organic functional layer 3 comprises one or more organic film layers; and a second electrode 4 is a metallic cathode. In one embodiment, the first electrode 2 and the second electrode 4 may be exchanged, namely the first electrode 2 is the metallic cathode, and the second electrode 4 is the transparent electrode of ITO, IGZO or the like.

The OLED display panel according to the present disclosure can be prepared by adopting a vacuum evaporation method.

Evaporation Preparation Process of OLED Display Panel

An anode substrate with an ITO film the thickness of which is 100 nm is subjected to ultrasonic cleaning with distilled water, acetone and isopropyl alcohol, dried in a baking oven, the surface of the anode substrate is subjected to UV treatment for 30 minutes, and then, the anode substrate is transferred into a vacuum evaporation cavity. The films of all layers is started to perform evaporation under the vacuum degree of $2 \times 10^{-6}$ Pa, a hole injection layer is formed by forming HATCN of 5 nm thick through evaporation, N,N'-diphenyl-N,N'-(1-naphthyl)-1,1'-biphenyl-4,4'-diamine (α-NPD) of 40 nm thick is formed through evaporation, and then, a hole transport layer (HTL) is formed through forming 4,4',4''-tri(carbazol-9-yl)triphenylamine (TCTA) of 10 nm thick through evaporation. A luminescent layer with the thickness of 30 nm is formed on the hole transport layer by taking the target compounds of the present disclosure as a doping material of the luminescent layer, taking 3,3'-di(N-carbazolyl)-1,1'-biphenyl (mCBP) as a host material of the luminescent layer and simultaneously performing evaporation of the doping material and the host material. Then, a hole barrier layer (HBL) with the thickness of 5 nm is formed by forming diphenyl[4-(triphenylsilyl)phenyl]phosphine oxide (TSPO1) on the luminescent layer through evaporation. An electron transport layer (ETL) with the thickness of 30 nm is formed by forming 4,7-diphenyl-1,10-phenanthroline (Bphen) on the hole barrier layer through evaporation. LiF of 2.5 nm thick and Al of 100 nm thick are sequentially formed on the electron transport layer through evaporation to serve as an electron injection layer (EIL) and a cathode, thereby an organic photo-electric device is produced.

The OLED display panel can also be prepared by adopting a solution processing method.

Specific steps for preparing a non-doped device comprise: ITO glass is subjected to ultrasonic cleaning twice separately with acetone, alkaline washing liquor, ultrapure water and isopropyl alcohol sequentially, and each time of ultrasonic cleaning is performed for 15 minutes, and then, treatment with an ozone washer is performed for 15 minutes. The glass substrate is coated with a PEDOT:PSS solution with the thickness of 40 nm through spin-coating, baked in a vacuum oven for 45 minutes at the temperature of 120° C., a TAPC layer and a mCP layer are separately prepared on PEDOT:PSS to serve as the hole transport layer and the electron barrier layer, and then, a toluene solution (with the concentration 12 mg/mL) of the compound according to the present disclosure is coated with the thickness of 40 nm to serve as a luminescent layer. The substrate is transferred into a vacuum chamber for thermal evaporation coating to prepare an electron transport layer (TmPyPb, 50 nm), an electron injection layer (LiF, 0.5-1 nm) and a cathode (Al, 100 nm), thereby forming the complete device.

Steps for preparing a doped device further comprise: an o-dichlorobenzene solution (with the concentration 12 mg/mL) of a host luminescent material and an o-dichlorobenzene solution (with the concentration 12 mg/mL) of a guest luminescent material are separately prepared, 50 μL (5%) of the guest material solution is transferred into the host material solution with a pipette, uniform magnetic stirring is performed, and then, a luminescent layer is coated. All other steps are the same as specific steps for preparing the non-doped device.

In one embodiment, the solution processing method is an ink jet printing method.

According to another embodiment of the present disclosure, a display device is provided and comprises the OLED display panel according to the present disclosure.

Figure 3:
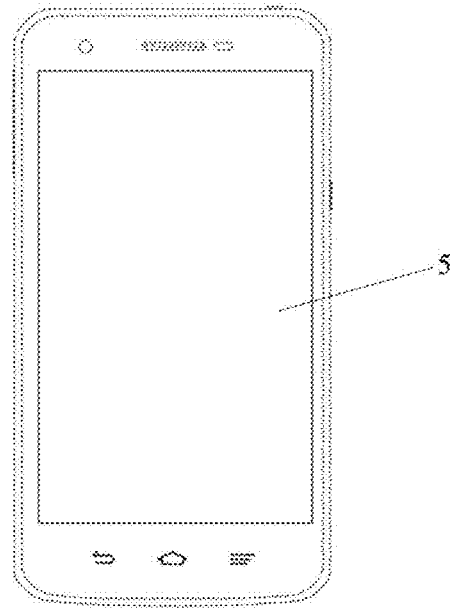
FIG. 3 is a schematic diagram of a mobile phone display screen.

The display device according to the present disclosure for example may be a mobile phone display screen, a computer display screen, a liquid crystal television display screen, etc., and the present embodiments do not make limits on this. FIG. 3 is a schematic diagram of a mobile phone display screen, and 5 represents the display screen.

Thus, it can be seen that the compound, the optional factors of the OLED display panel and the display device according to the present disclosure are varied, and different examples can be combined according to claims of the present disclosure. Examples of the present disclosure are only intended to specifically describe the present disclosure, rather than limit the present disclosure.

The present disclosure will be further described below with reference to the OLED display panel containing the compound of the present disclosure as an example.

Synthesis of Compound P1:

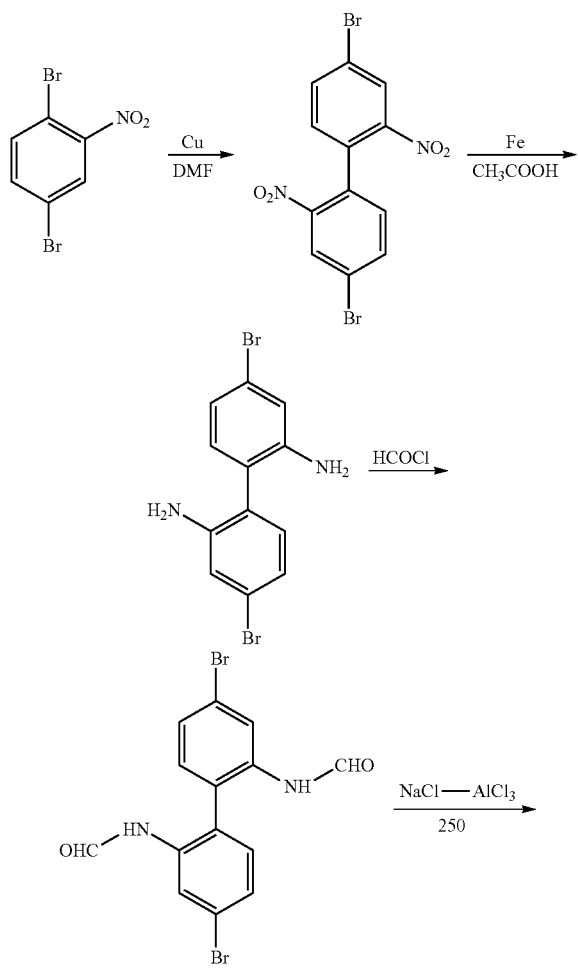

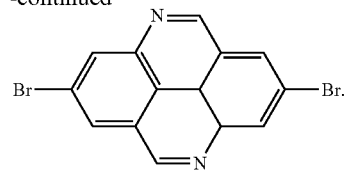

In a round-bottomed flask of 250 ml, 2,5-dibromonitrobenzene (15 mmol) and Cu (7 mmol) are added into dried DMF (100 ml), a reaction is carried out for 3.5 hours at a temperature of 125° C. in a nitrogen gas atmosphere, the obtained intermediate mixed solution is added into water, then, filtered with a diatomite pad, filter liquor is extracted with dichloromethane, then washed with water, and dried with anhydrous magnesium sulfate, after filtering and evaporation, a crude product is purified through silica-gel column chromatography, thereby obtaining an intermediate product 4,4-dibromo-2,2-dinitrobenzene.

In a round-bottomed flask of 250 ml, the 4,4-dibromo-2, 2-dinitrobenzene (15 mmol) and Fe (0.225 mol) are added into dried acetic acid (100 ml), a reaction is carried out for 1.0 hour at a temperature of 80° C. in a nitrogen gas atmosphere, and metal residues are directly filtered off from the obtained intermediate mixed solution to obtain a reaction solution for a next-step reaction.

In a round-bottomed flask of 250 ml, acetyl chloride (75 mmol), the reaction solution obtained in the previous step and triethylamine (5 ml) are added into dried dichloromethane (100 ml), a reaction is carried out over night at a temperature of 0° C. in a nitrogen gas atmosphere, the obtained intermediate is added into water, then, filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product, N,N'-(4,4'-dibromo-[1,1'-biphenyl]-2,2'-diyl)diacetaldehyde.

In a round-bottomed flask of 250 ml, the N,N'-(4,4'-dibromo-[1,1'-biphenyl]-2,2'-diyl)diacetaldehyde (15 mmol) is added, aluminum chloride and sodium chloride (0.15 mol) are carefully added, a reaction is carried out for 8 hours at a temperature of 250° C. in a nitrogen gas atmosphere, the obtained intermediate is added into water, then, filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product 4,4'-dibromophenanthridine

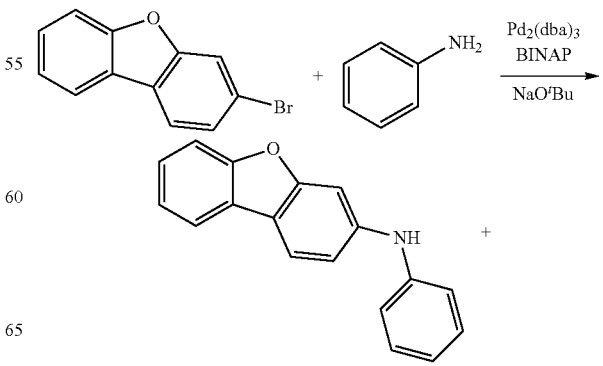

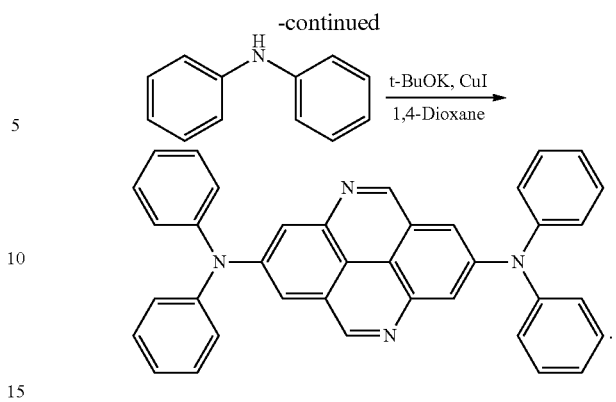

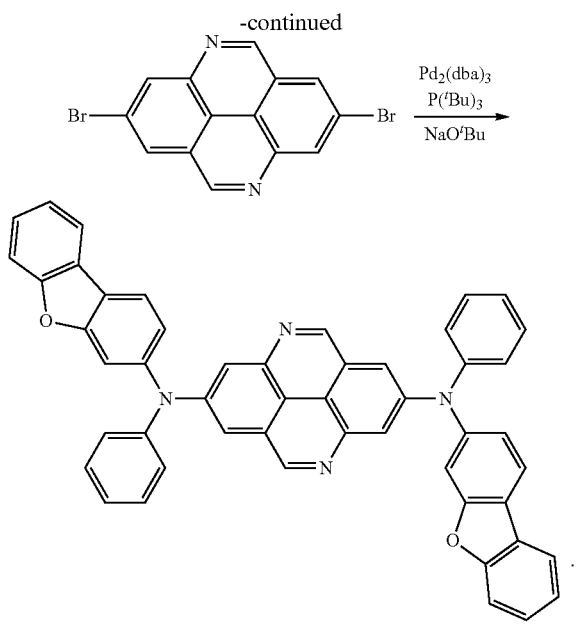

In a round-bottomed flask of 250 ml, 3-bromo-dibenzofuran (15 mmol), aniline (15 mmol), 10 mol % Pd$_2$(dba)$_3$, sodium tert-butoxide (100 mmol) and BINAP (24 mmol) are added into dried toluene (100 ml), refluxed for 48 hours in a nitrogen gas atmosphere, the obtained intermediate is cooled to room temperature, added into water, and then filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product dibenzofuran-3-yl-phenyl-amine.

In a round-bottomed flask of 250 ml, the dibenzofuran-3-yl-phenyl-amine (30 mmol), the 4,4'-dibromophenanthridine (15 mmol), 20 mol % Pd$_2$(dba)$_3$, sodium tert-butoxide (200 mmol) and BINAP (48 mmol) are added into dried toluene (100 ml), refluxed for 48 hours in a nitrogen gas atmosphere, the obtained intermediate is cooled to room temperature, added into water, then filtered with a diatomite pad, the filter liquor is extracted with dichloromethane, washed with water, and dried with anhydrous magnesium sulfate, after filtering and evaporation are performed, a crude product is purified through silica-gel column chromatography, thereby obtaining the final product P1.

Elemental analysis on the compound P1 (molecular formula C50H30N4O2): theoretical value: C, 83.56; H, 4.18; N, 7.80; O, 4.46. Test value: C, 83.56; H, 4.18; N, 7.80; O, 4.46. ESI-MS(m/z)(M+) obtained through liquid chromatography-mass spectrometry: a theoretical value is 718.24, and a test value is 718.25.

Synthesis of Compound P25:

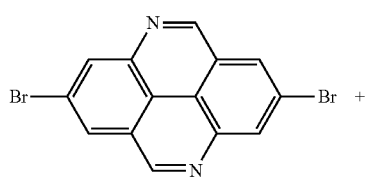

In a round-bottomed flask of 250 ml, 4,4'-dibromophenanthridine (15 mmol), cupric iodide (30 mmol), potassium tert-butoxide (100 mmol), 1,2-diaminocyclohexane (24 mmol) and diphenylamine (50 mmol) are added into dried 1,4-dioxane (100 ml), refluxed for 48 hours in a nitrogen gas atmosphere, the obtained intermediate is cooled to room temperature, added into water, and filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product P25.

Elemental analysis on the compound P25 (molecular formula C$_{38}$H$_{26}$N$_4$): theoretical value: C, 84.76; H, 4.83; N, 10.41. Test value: C, 84.76; H, 4.83; N, 10.41. ESI-MS(m/z)(M+) obtained through liquid chromatography-mass spectrometry: a theoretical value is 538.22, and a test value is 538.21.

Synthesis of Compound P28:

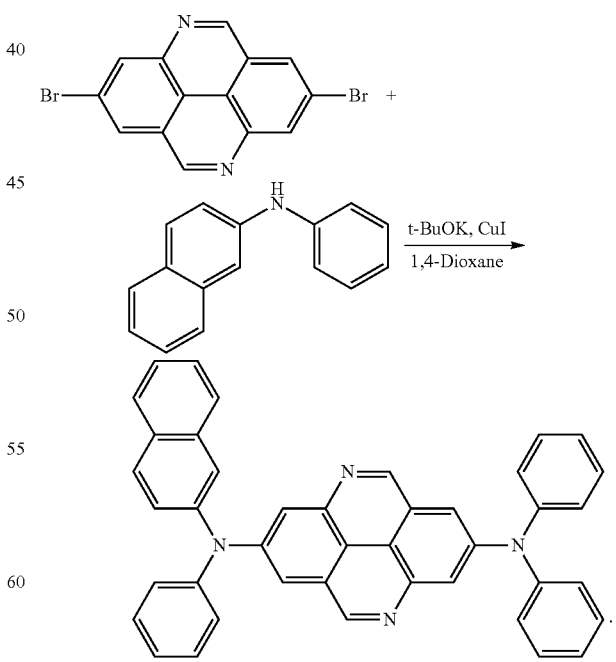

In a round-bottomed flask of 250 ml, 4,4'-dibromophenanthridine (15 mmol), cupric iodide (30 mmol), potassium tert-butoxide (100 mmol), 1,2-diaminocyclohexane (24 mmol) and naphthyl-2-phenylamine (50 mmol) are added into dried 1,4-dioxane (100 ml), refluxed for 48 hours in a nitrogen gas atmosphere, the obtained intermediate is cooled to room temperature, added into water, and then filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product P28.

Elemental analysis on the compound P28 (molecular formula $C_{46}H_{30}N_4$): theoretical value: C, 86.52; H, 4.70; N, 8.78. Test value: C, 86.52; H, 4.70; N, 8.78. ESI-MS(m/z) (M+) obtained through liquid chromatography-mass spectrometry: a theoretical value is 638.25, and a test value is 638.24.

Synthesis of Compound P30:

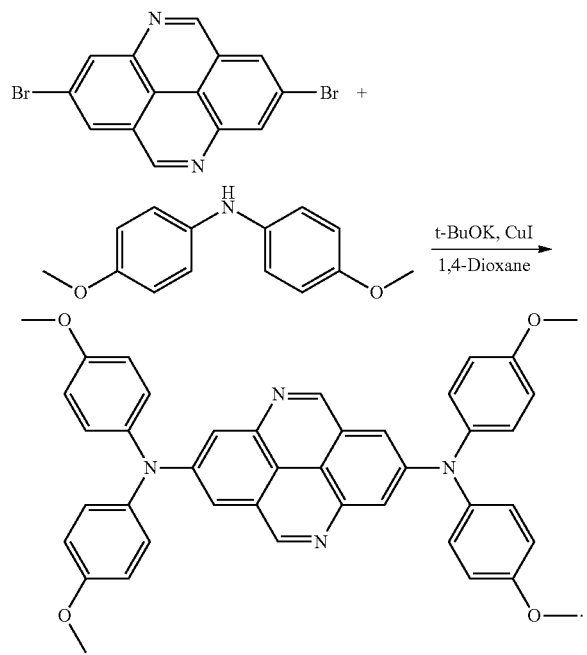

In a round-bottomed flask of 250 ml, 4,4'-dibromophenanthridine (15 mmol), cupric iodide (30 mmol), potassium tert-butoxide (100 mmol), 1,2-diaminocyclohexane (24 mmol) and bis(4-methoxyphen)ylamine (50 mmol) are added into dried 1,4-dioxane (100 ml), refluxed for 48 hours in a nitrogen gas atmosphere, the obtained intermediate is cooled to room temperature, added into water, and then filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product P30.

Elemental analysis on the compound P30 (molecular formula $C_{42}H_{34}N_4O_4$): theoretical value: C, 76.60; H, 5.17; N, 8.50; O, 9.73. Test value: C, 76.60; H, 5.17; N, 8.50; O, 9.73. ESI-MS(m/z)(M+) obtained through liquid chromatography-mass spectrometry: a theoretical value is 658.26, and a test value is 658.24.

Synthesis of Compound P55:

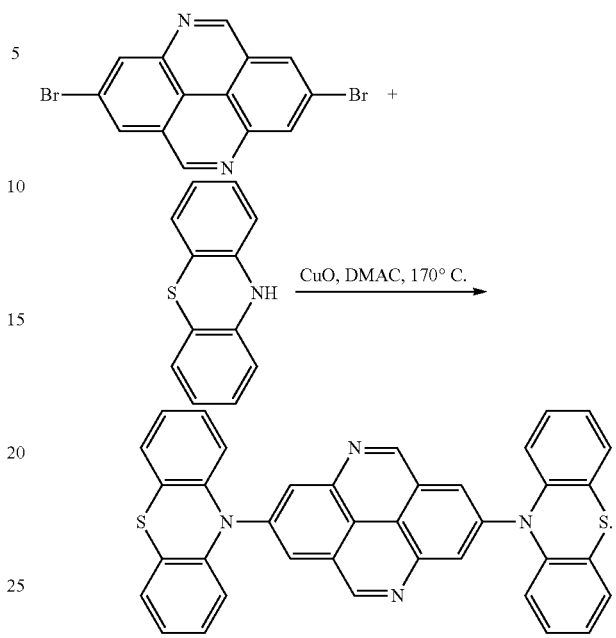

In a round-bottomed flask of 250 mL, 4,4'-dibromophenanthridine (15 mmol), 10H-phenothiazine (30 mmol), copper oxide (40 mmol), DMAC (20 mL) and toluene (100 mL) are refluxed for 48 hours in a nitrogen gas atmosphere, the obtained intermediate is cooled to room temperature, added into water, and then filtered with a diatomite pad, the filter liquor is extracted with dichloromethane, then washed with water, and dried with anhydrous magnesium sulfate, after filtering and evaporation are performed, a crude product is purified through silica-gel column chromatography, thereby obtaining an intermediate product P55.

Elemental analysis on the compound P55 (molecular formula $C_{38}H_{22}N_4S_2$): theoretical value: C, 76.25; H, 3.68; N, 9.37; S, 10.70. Test value: C, 76.25; H, 3.68; N, 9.37; S, 10.70. ESI-MS(m/z)(M+) obtained through liquid chromatography-mass spectrometry: a theoretical value is 598.13, and a test value is 598.12.

Other compounds are also obtained by adopting similar synthesis methods.

The compounds and the structures thereof involved in the examples of the present disclosure are as follows:

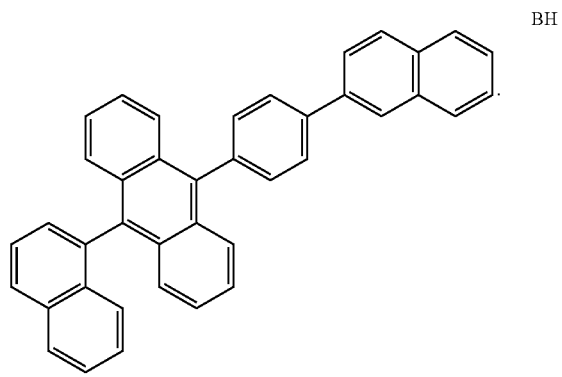 [SMILES: c1ccc2cc(-c3ccc(-c4c5ccccc5c(-c5cccc6ccccc56)c5ccccc45)cc3)ccc2c1]

BH

Compounds employed in comparative examples have structures as below:

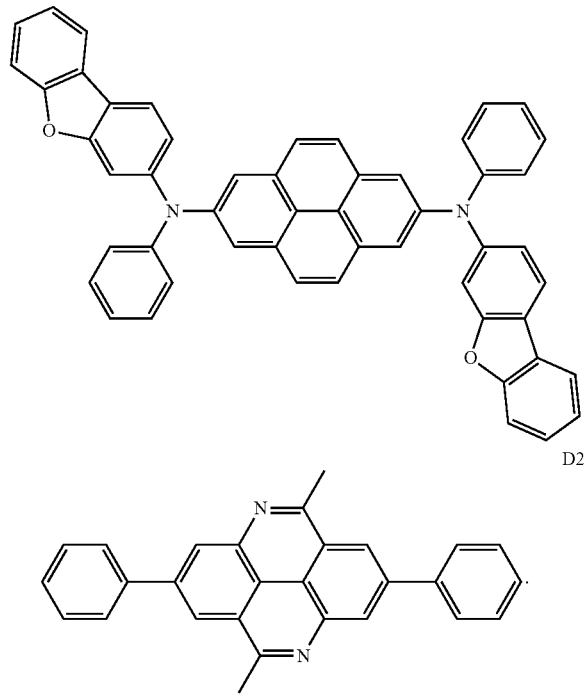

FIG. 1 shows an orbit distribution condition of the compound P1, and, (a) in FIG. 1 is a HOMO energy level distribution diagram of the compound P1, and (b) in FIG. 1 is a LUMO energy level distribution diagram of the compound P1.

In view of the compounds of the present disclosure employed in the examples, optimization and calculation are performed by using a density functional theory (DFT) and utilizing a program package Gaussian 09 in a B3LYP/6-31G (d) calculation level, to obtain distribution conditions of molecular frontier orbits; and meantime, singlet energy levels $S_1$ and triplet energy levels $T_1$ of molecules are subjected to analog calculation on the basis of a time-dependent density functional theory (TD-DFT), and the results are shown in a table 1, and, $S_1$ represents a singlet energy level, $T_1$ represents a triplet energy level, Eg=HOMO-LUMO, and a numerical value of Eg is an absolute value.

TABLE 1

Analog calculation results of compounds

| Embodiment | Compound | HOMO (ev) | LUMO (ev) | $S_1$ (ev) | $T_1$ (ev) | Eg (ev) |
|---|---|---|---|---|---|---|
| 1 | P1 | −4.899 | −1.984 | 2.646 | 2.073 | 2.92 |
| 2 | P5 | −4.932 | −1.988 | 2.738 | 2.091 | 2.94 |
| 3 | P25 | −4.926 | −1.976 | 2.674 | 2.094 | 2.95 |
| 4 | P28 | −4.912 | −2.012 | 2.638 | 2.081 | 2.90 |
| 5 | P30 | −4.548 | −1.783 | 2.510 | 1.950 | 2.77 |
| 6 | P45 | −4.936 | −1.876 | 2.684 | 2.099 | 3.06 |
| 7 | P49 | −5.543 | −2.545 | 2.693 | 2.232 | 3.00 |
| 8 | P55 | −5.079 | −2.367 | 2.416 | 2.201 | 2.71 |

From the table 1, it is observed that the compounds prepared by the examples of the present disclosure have greater Eg values and higher triplet energy levels $T_1$, can serve as blue light emitting materials and have proper HOMO and LUMO values, a hole transport layer and an electron transport layer can be better matched, and thus, the gathering of holes and electrons on a luminescent layer and balancing of transporting of a current carrier are facilitated; and meanwhile, the compounds have higher singlet and triplet energy levels and excellent thermal stability and film stability, so that the increase of luminous efficiency is facilitated.

Taking the compounds P1, P5, P25, P28, P30, P45, P49 and P55 as luminescent materials, non-doped devices N1 to N8 are designed by adopting a vacuum evaporation method and have structures as follows: ITO (100 nm)/α-NPD (40 nm)/TCTA (10 nm)/P (40 nm)/TmPyPb (50 nm)/LiF (0.5 nm)/Al (100 nm), and results are shown in a table 2.

TABLE 2

Property results of non-doped devices prepared by vacuum evaporation method

| Device | Luminescent material | $V_{on}$ [V] | E/CIEy | $EQE_{(max)}$ (%) | Lifetime LT95 |
|---|---|---|---|---|---|
| N1 | P1 | 3.90 | 79.1 | 6.6 | 131.7 |
| N2 | P5 | 3.79 | 80.4 | 6.4 | 130.5 |
| N3 | P25 | 3.84 | 70.8 | 14.3 | 129.6 |
| N4 | P28 | 3.79 | 79.7 | 7.0 | 130.9 |
| N5 | P30 | 3.82 | 76.9 | 7.8 | 131.7 |
| N6 | P45 | 3.78 | 85.5 | 8.2 | 131.5 |
| N7 | P49 | 3.73 | 86.1 | 12.3 | 130.8 |
| N8 | P55 | 3.85 | 75.4 | 9.7 | 134.6 |
| M1 | D1 | 4.08 | 67.8 | 6.3 | 115.6 |
| M2 | D2 | 4.16 | 69.6 | 5.9 | 100.1 |

From the table 2, it is observed that optical devices employing the compounds of the present disclosure are lower in driving voltage, higher in luminous efficiency and longer in service life. Compared with the comparative example M1, in an aza-containing pyrene structure of the present disclosure, conjugation is broken off by a nitrogen atom, a molecular excited state can be improved, and thus, the brightness is improved; and compared with the comparative example M2, an arylamine three-dimensional structure can improve a thermal effect caused by molecular aggregation and accumulation, so that the lifetime is prolonged.

Taking the compounds P1, P5, P25, P28, P30, P45, P49 and P55 as luminescent guest materials and taking BH as a host material, doped devices N9 to N16 are designed by adopting a vacuum evaporation method and have structures as follows: ITO (100 nm)/α-NPD (40 nm)/TCTA (10 nm)/ BH:P (40 nm, 5%)/TmPyPb (50 nm)/LiF (0.5 nm)/Al (100 nm), and results are shown in a table 3.

TABLE 3

Property results of doped devices prepared by vacuum evaporation method

| Device | Fluorescence dopant | $V_{on}$ [V] | E/CIEy | $EQE_{(max)}$ (%) |
|---|---|---|---|---|
| N9 | P1 | 3.80 | 80.1 | 6.7 |
| N10 | P5 | 3.71 | 80.5 | 6.5 |
| N11 | P25 | 3.82 | 79.8 | 15.3 |
| N12 | P28 | 3.78 | 79.6 | 7.2 |

TABLE 3-continued

Property results of doped devices prepared by vacuum evaporation method

| Device | Fluorescence dopant | $V_{on}$ [V] | E/CIEy | $EQE_{(max)}$ (%) |
|---|---|---|---|---|
| N13 | P30 | 3.82 | 76.8 | 7.6 |
| N14 | P45 | 3.76 | 85.3 | 8.4 |
| N15 | P49 | 3.71 | 87.1 | 11.3 |
| N16 | P55 | 3.75 | 75.9 | 9.8 |
| M3 | D1 | 4.06 | 69.9 | 6.5 |
| M4 | D2 | 4.14 | 67.6 | 6.0 |

From the table 3, it is observed that compared with the doped device comparative examples M3 and M4, optical devices employing the compounds of the present disclosure are lower in driving voltage, higher in current efficiency and higher in brightness. Compared with the comparative examples M3 and M4, the driving voltage is lower than 3.82V and is increased by 7.7%; and the luminous efficiency is higher than 75 Cd/A and is increased by 10%.

What is claimed is:

1. A compound, wherein the compound has a structure represented by a formula (I) or a formula (II):

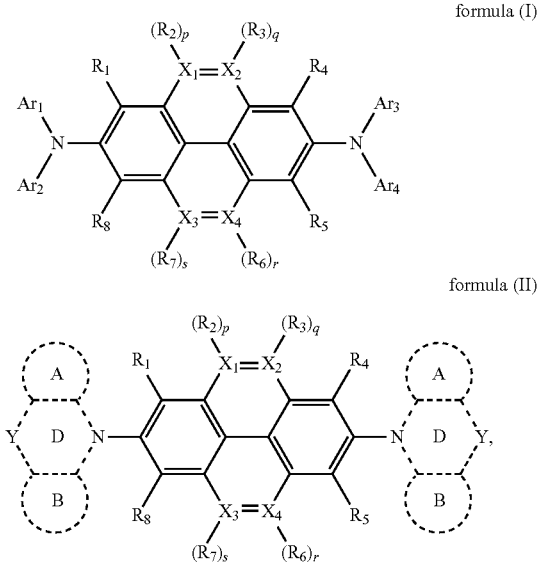

in the formula (I) and the formula (II), $X_1$-$X_4$ each are independently selected from a C atom or a N atom, and at least two of $X_1$-$X_4$ are N atoms; and $R_1$-$R_8$ each are independently selected from at least one of a hydrogen atom, methyl-substituted or unsubstituted C1-C20 alkyl, unsubstituted C3-C20 cycloalkyl, unsubstituted C3-C20 heterocyclyl, substituted or unsubstituted C6-C40 aryl, unsubstituted C4-C40 heteroaryl, unsubstituted C10-C60 condensed aryl or unsubstituted C10-C60 condensed heteroaryl;

p, q, r and s each are independently selected from 0 or 1;

in the formula (I), $Ar_1$-$Ar_4$ each are independently selected from at least one of substituted or unsubstituted aryl with the number of carbon atoms to be C6-C30, substituted or unsubstituted heterocyclyl with the number of carbon atoms to be C5-C20, alkylsilicyl with the number of carbon atoms to be C3-C30, or arylsilicyl with the number of carbon atoms to be C8-C30; and in the formula (II), Y is selected from a direct bond, a S atom, an O atom, a N atom or a C atom; A and B each are independently selected from at least one of substituted or unsubstituted C6-C40 aryl, substituted or unsubstituted C4-C40 heteroaryl, and D is selected from a N-atom-containing five-membered ring or six-membered ring; wherein when D is the N-atom-containing five-membered ring, Y is a direct bond; when D is the N-atom-containing six-membered ring, Y is selected from a S atom, an O atom, a N atom or a C atom.

2. The compound according to claim 1, wherein in $X_1$-$X_4$, $X_1$ and $X_2$ are N atoms, and $X_3$ and $X_4$ are C atoms.

3. The compound according to claim 1, wherein in $X_1$-$X_4$, $X_1$ and $X_3$ are N atoms, and $X_2$ and $X_4$ are C atoms.

4. The compound according to claim 1, wherein in $X_1$-$X_4$, $X_1$ and $X_4$ are N atoms, and $X_2$ and $X_3$ are C atoms.

5. The compound according to claim 1, wherein $R_3$ and $R_7$ are the same, and $R_2$ and $R_6$ are the same.

6. The compound according to claim 1, wherein $R_1$ and $R_5$ are the same, and $R_4$ and $R_8$ are the same.

7. The compound according to claim 1, wherein $Ar_1$ and $Ar_4$ are the same, and $Ar_2$ and $Ar_3$ are the same.

8. The compound according to claim 1, wherein $R_1$-$R_8$ each are independently selected from C1-C20 alkyl and C3-C20 cycloalkyl.

9. The compound according to claim 1, wherein at least two of p, q, r and s are 0.

10. The compound according to claim 1, wherein in $R_1$-$R_8$, the aryl with the number of carbon atoms to be C6-C30 is selected from one or more of phenyl, biphenyl, 9,9-fluorenyl, terphenyl, naphthyl, anthryl, phenanthryl, 9,10-benzophenanthryl, 1,2-benzophenanthryl, acenaphthylenyl, perylenyl, pyrenyl and indenyl; and the heterocyclyl with the number of carbon atoms to be C5-C20 is selected from one or more of furyl, thienyl, pyrryl, oxazolyl, thiazolyl, pyrazolyl, pyranyl, imidazolyl, pyridyl, pyrazinyl, pyrimidyl, 1,3,4-oxadiazolyl, 1,2,4-triazolyl, 1,3,5-triazinyl, indolyl, benzimidazolyl, dibenzofuryl, dibenzothienyl, carbazolyl, quinolyl, quinoxalyl, ortho-phenanthrolinyl, phenazinyl and pyridazinyl.

11. The compound according to claim 1, wherein the alkylsilicyl with the number of carbon atoms to be C3-C30 is selected from trimethyl silicyl and triethyl silicyl, and the arylsilicyl with the number of carbon atoms to be C8-C30 is selected from phenyl trimethyl silicyl, phenyl triethyl silicyl.

12. The compound according to claim 1, wherein in $R_1$-$R_8$, the aryl with the number of carbon atoms to be C6-C30 is selected from at least one of phenyl, naphthyl, biphenyl, 9,9-fluorenyl and terphenyl; and the heterocyclyl with the number of carbon atoms to be C5-C20 is selected from at least one of dibenzofuryl, dibenzothienyl and pyridyl.

13. The compound according to claim 1, wherein the compound has a structure represented by a formula (II-1)

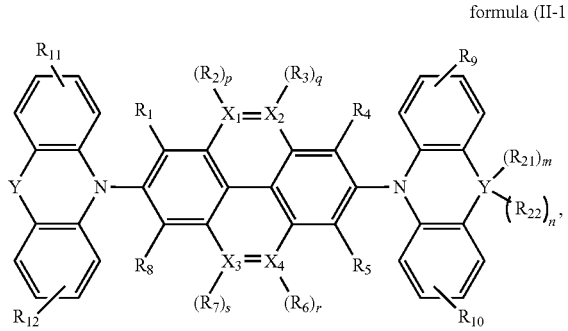

formula (II-1)

wherein, $X_1$-$X_4$ each are independently selected from a C atom or a N atom, and at least two of $X_1$-$X_4$ are N atoms; and $R_1$-$R_8$ each are independently selected from at least one of a hydrogen atom, methyl-substituted or unsubstituted C1-C20 alkyl, unsubstituted C3-C20 cycloalkyl, unsubstituted C3-C20 heterocyclyl, unsubstituted C6-C40 aryl, unsubstituted C4-C40 heteroaryl, unsubstituted C10-C60 condensed aryl, or unsubstituted C10-C60 condensed heteroaryl;

p, q, r, s, m and n each are independently selected from 0 or 1; and

Y is selected from a S atom, an O atom, a N atom or a C atom; $R_9$, $R_{10}$, $R_{11}$ and $R_{12}$ each are independently selected from at least one of a hydrogen atom, C1-C6 alkyl, C1-C6 alkoxy, —$CF_3$, —S—$CH_3$ and —CN—; and $R_{21}$ and $R_{22}$ each are independently selected from at least one of a hydrogen atom, C1-C6 alkyl and C1-C6 alkoxy.

14. The compound according to claim 1, wherein Y is an S atom.

15. The compound according to claim 1, wherein the compound has a structure represented by a formula (II-2)

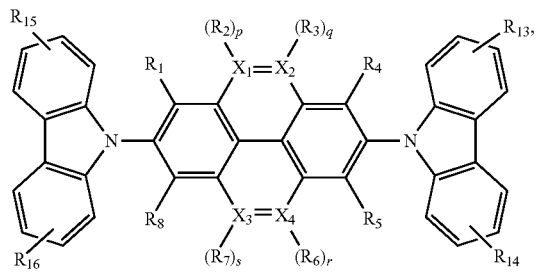

formula (II-2)

wherein, $X_1$-$X_4$ each are independently selected from a C atom or a N atom, and at least two of $X_1$-$X_4$ are N atoms; and $R_1$-$R_8$ each are independently selected from at least one of a hydrogen atom, methyl-substituted or unsubstituted C1-C20 alkyl, unsubstituted C3-C20 cycloalkyl, unsubstituted C3-C20 heterocyclyl, substituted or unsubstituted C6-C40 aryl, unsubstituted C4-C40 heteroaryl, unsubstituted C10-C60 condensed aryl, or unsubstituted C10-C60 condensed heteroaryl;

p, q, r and s each are independently selected from 0 or 1; and $R_{13}$, $R_{14}$, $R_{15}$ and $R_{16}$ each are independently selected from at least one of a hydrogen atom, C1-C6 alkyl, C1-C6 alkoxy, —$CF_3$, —S—$CH_3$ and —CN—.

16. The compound according to claim 1, wherein the compound is selected from any one of

P1

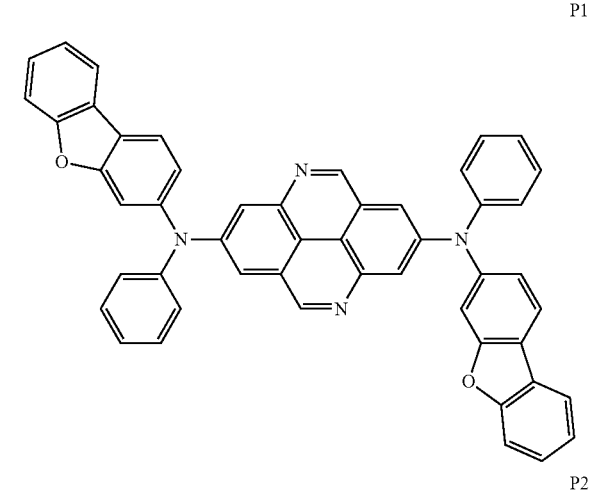

P2

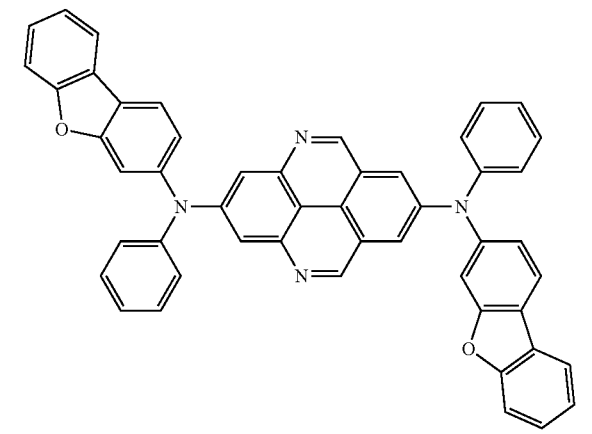

P3

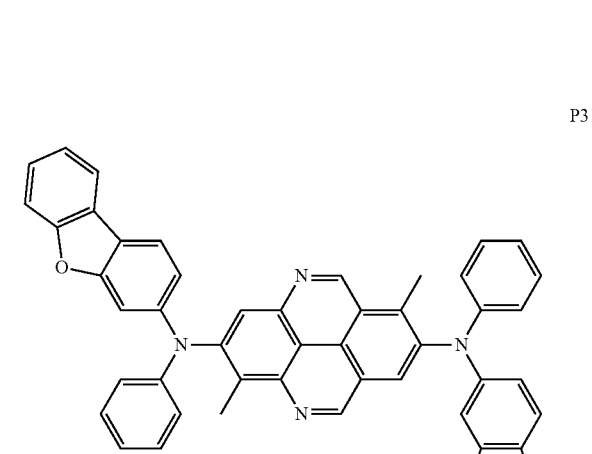

P4
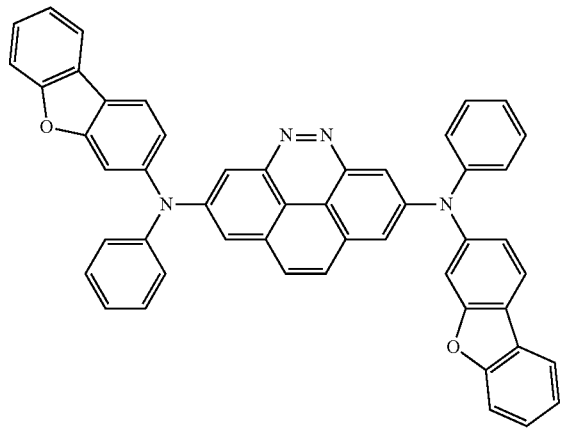
P5
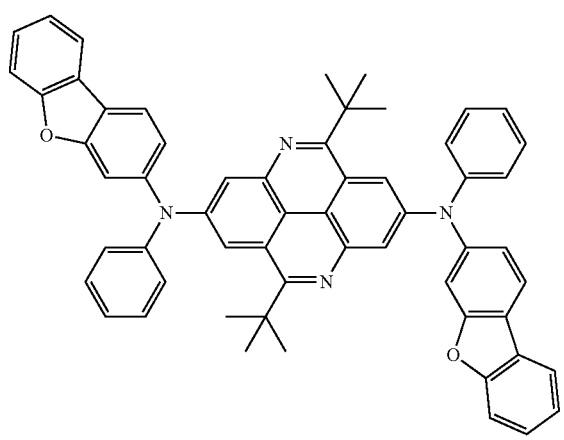
P6
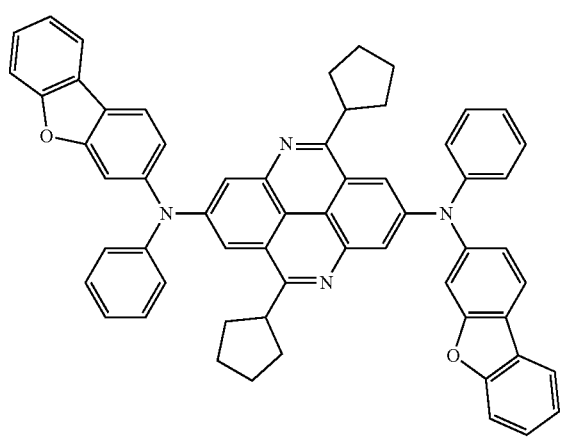
P7
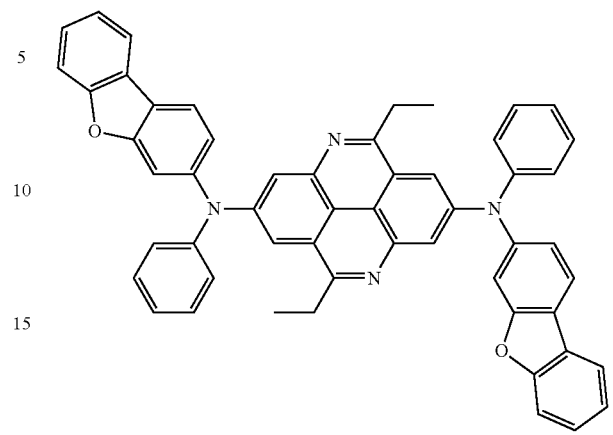
P8
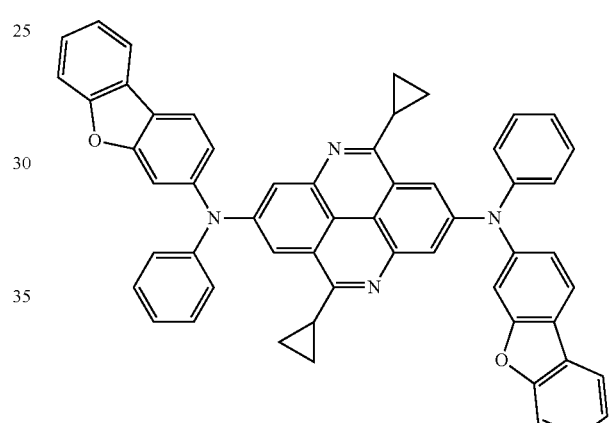
P9
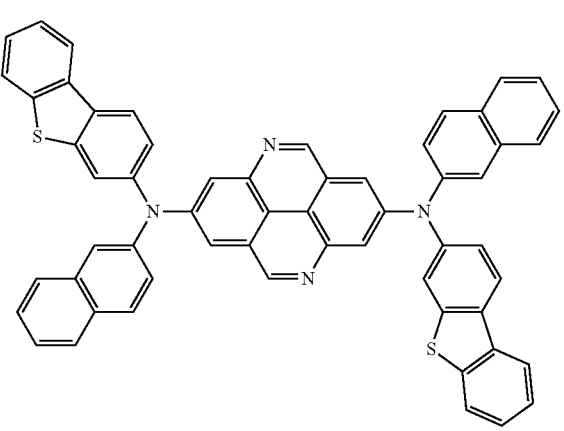

P10
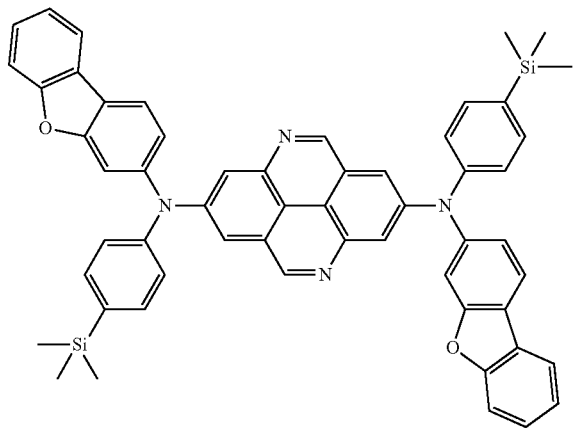
P11
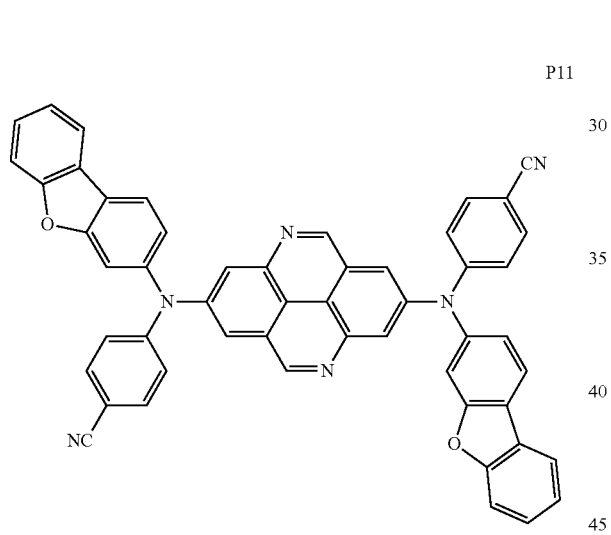
P12
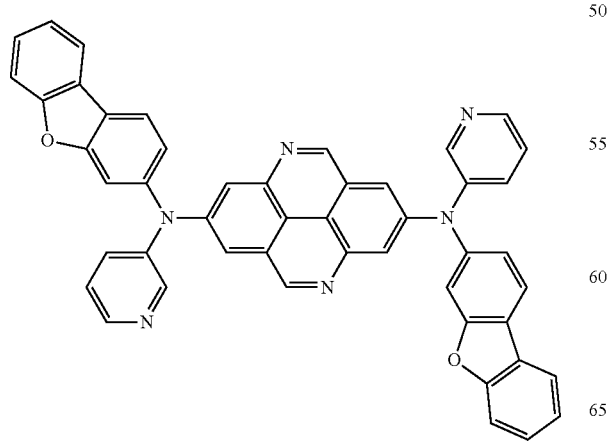
P13
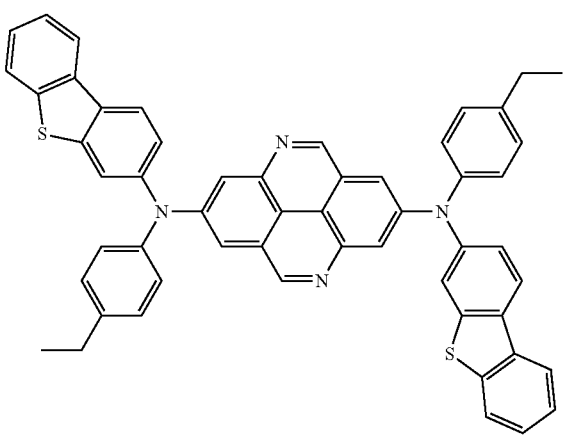
P14
P15
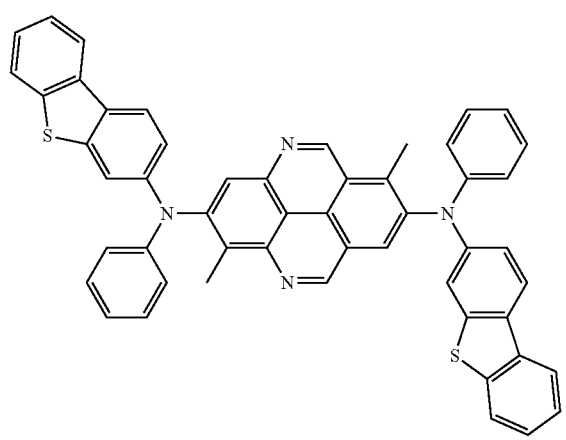

P16
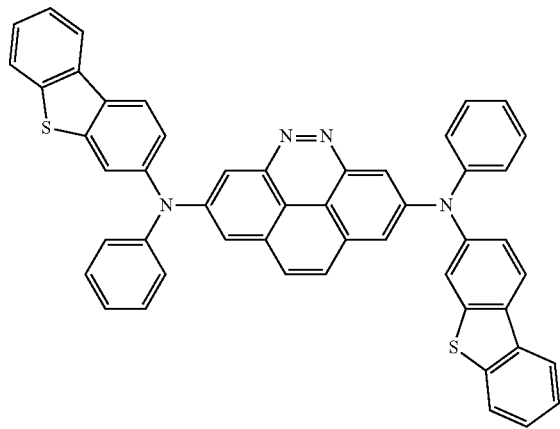
P19
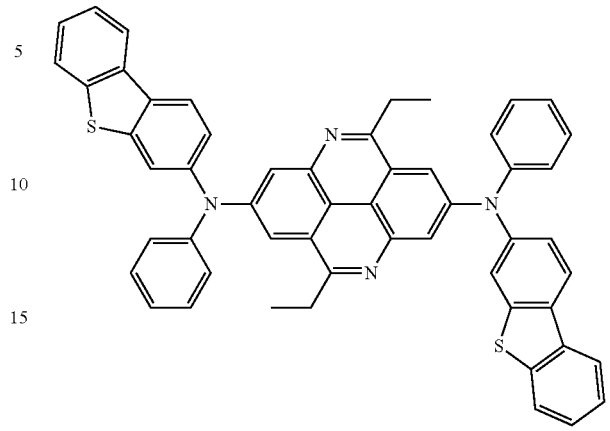
P17
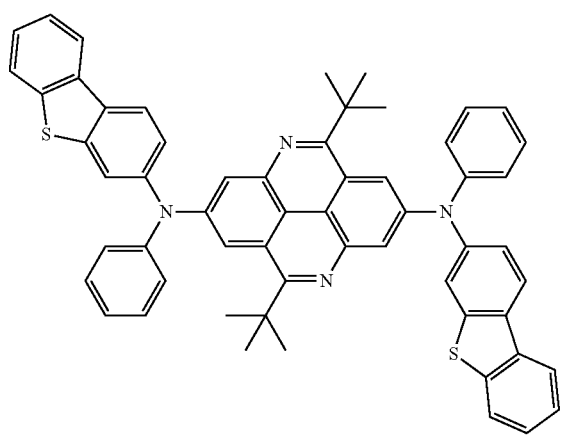
P20
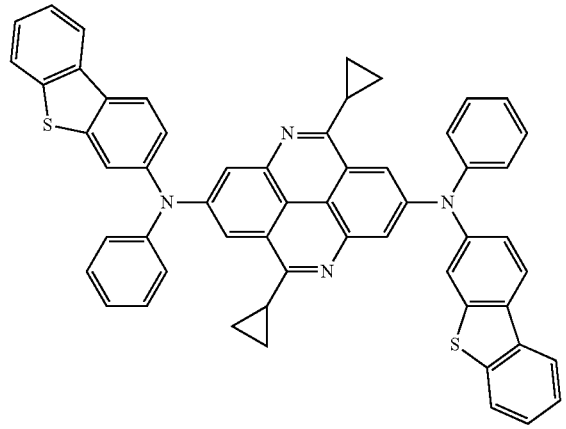
P18
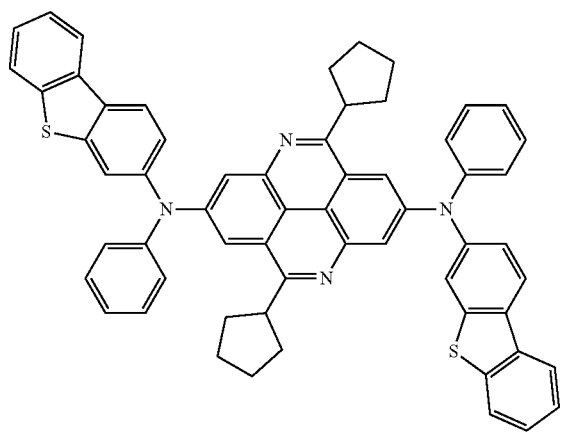
P21
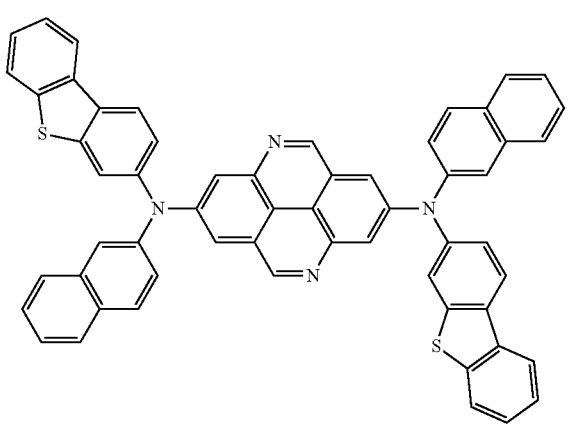

-continued
P22
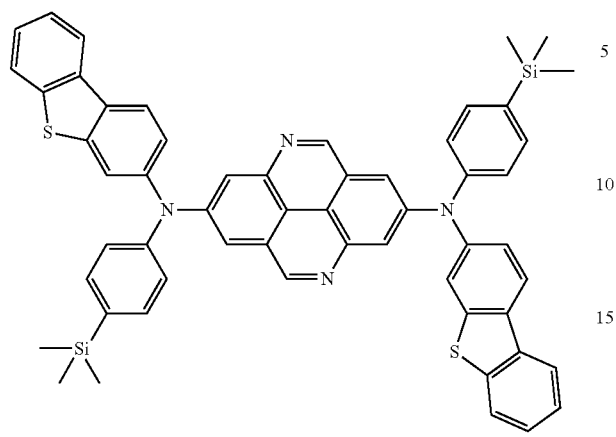
P23
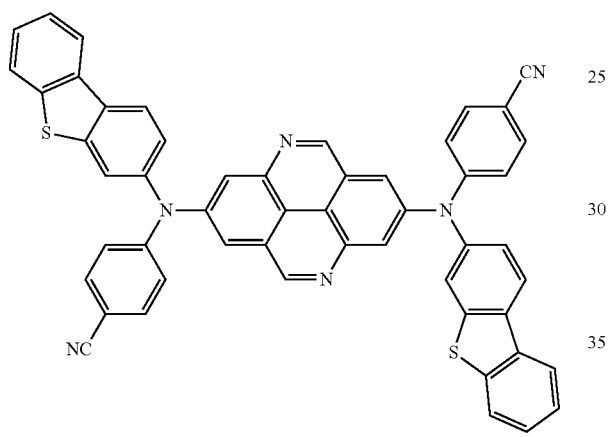
P24
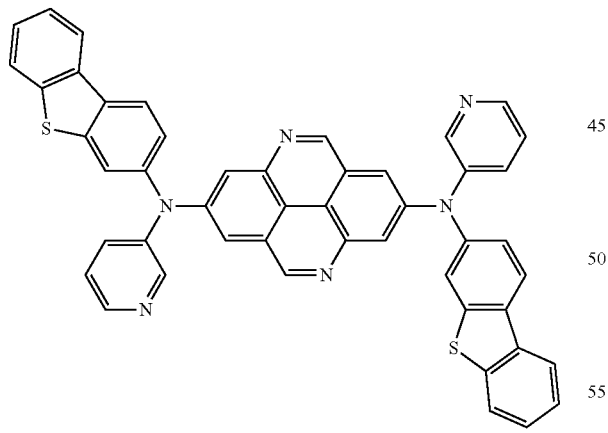
P25
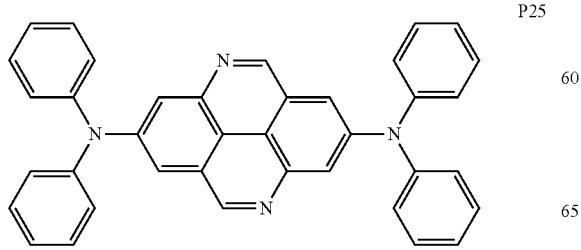
-continued
P26
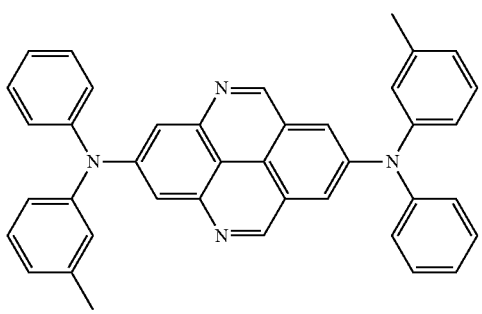
P27
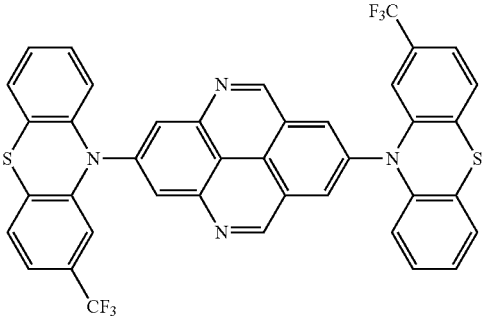
P28
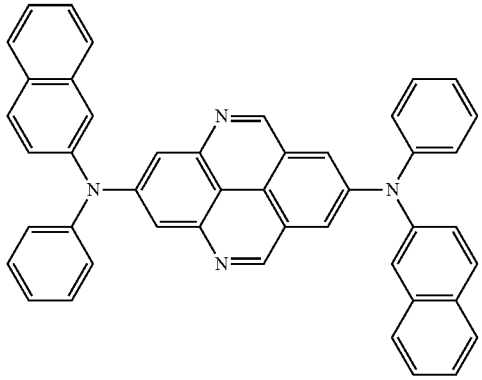
P29
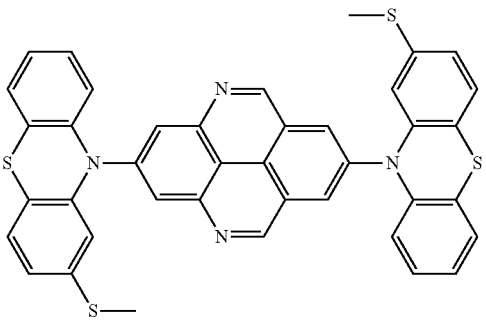

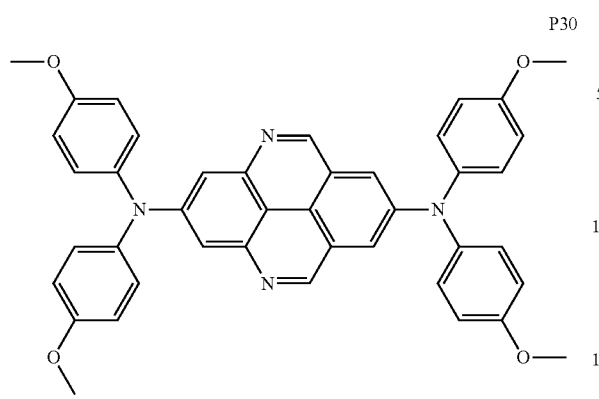
P30
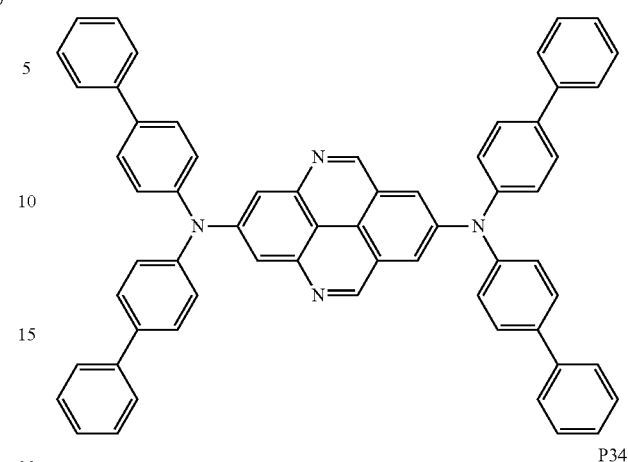
P33
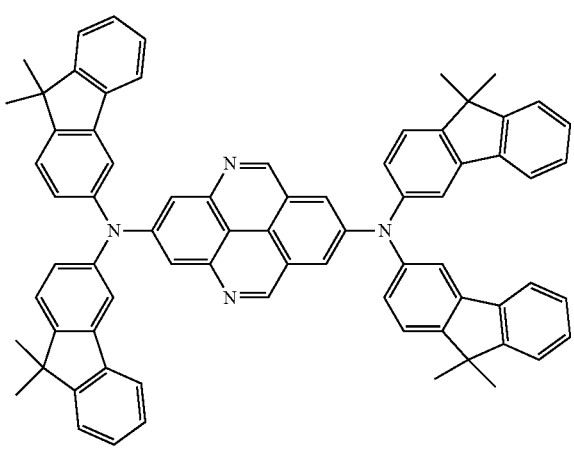
P31
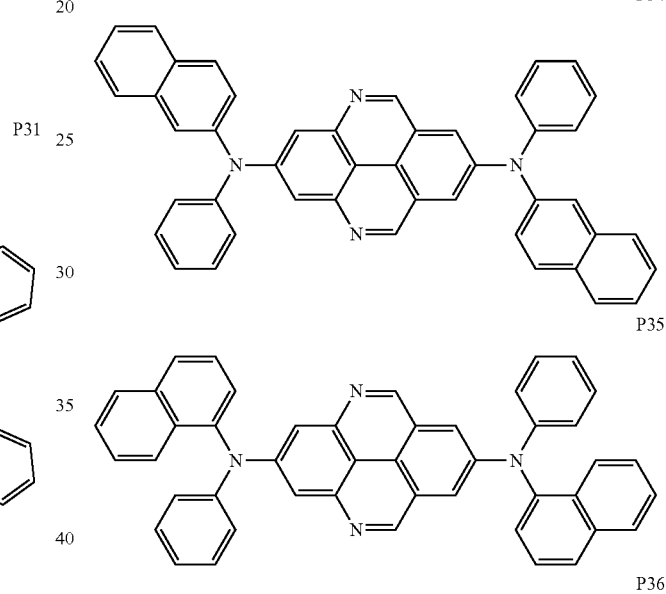
P34
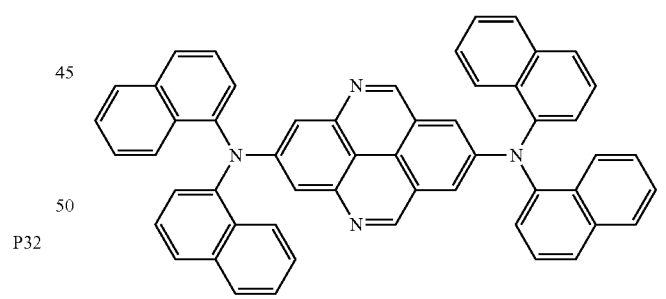
P35
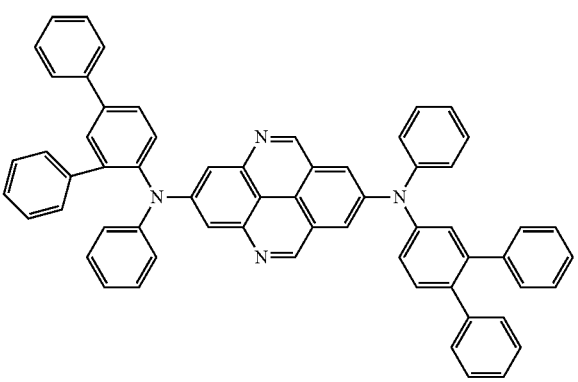
P32
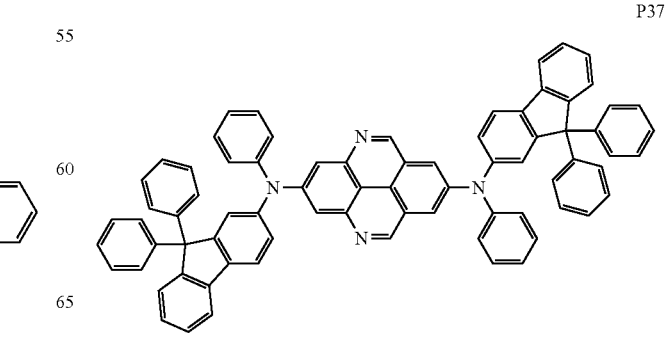
P36
P37

-continued
P38
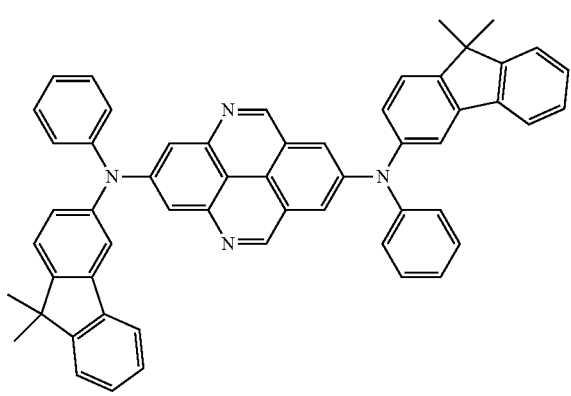
P39
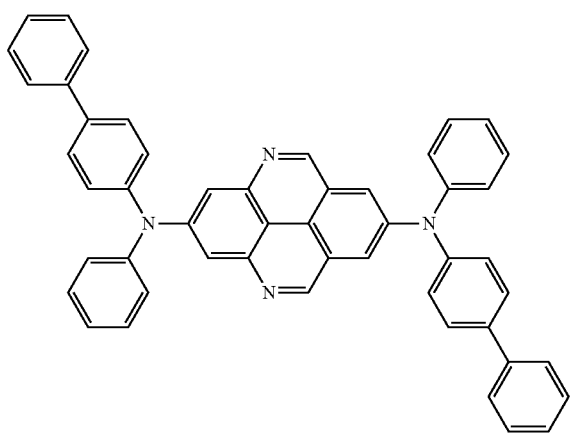
P40
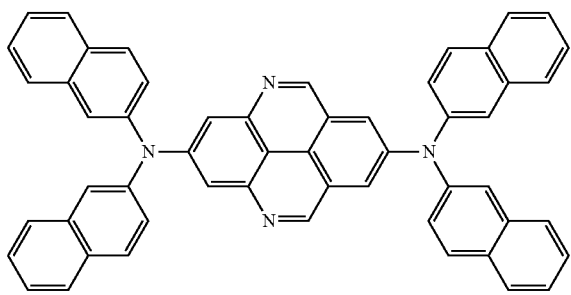
P41
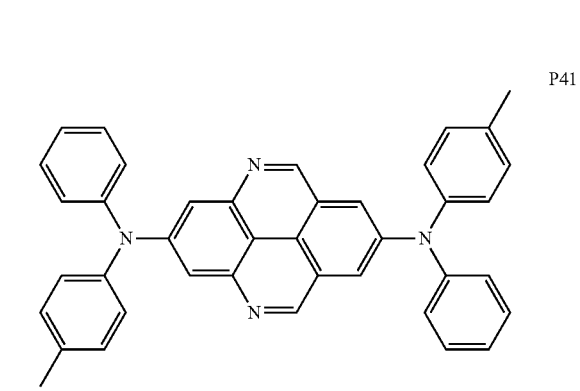
-continued
P42
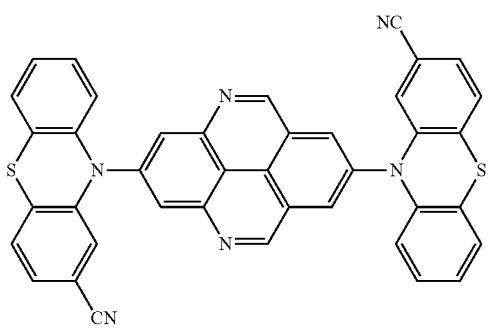
P43
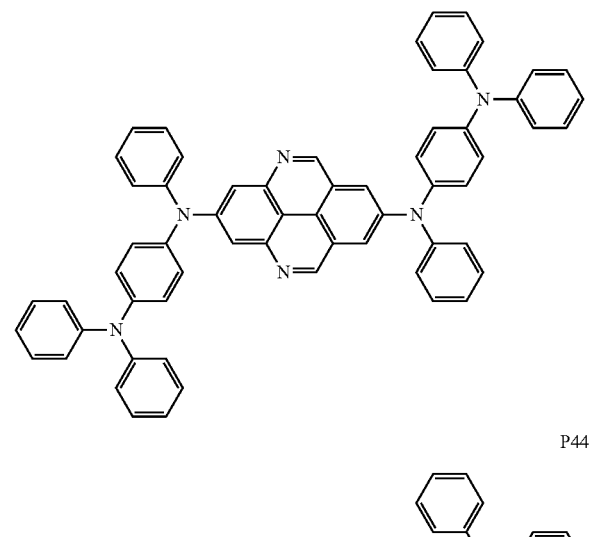
P44
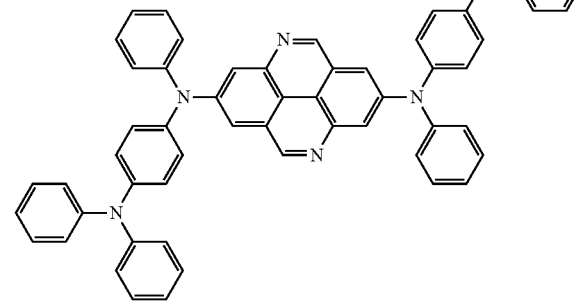
P45
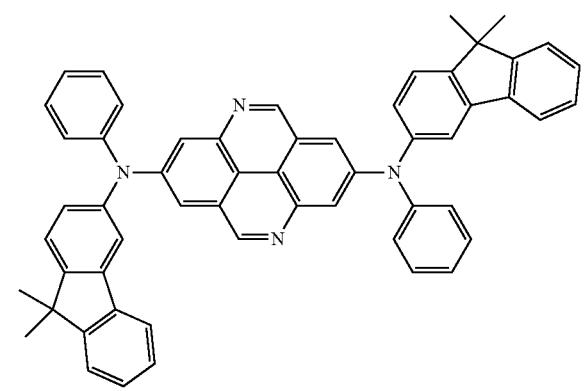

P46 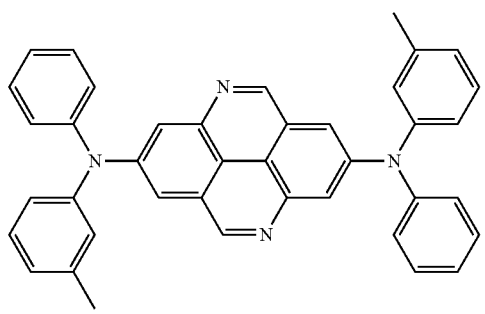
P47 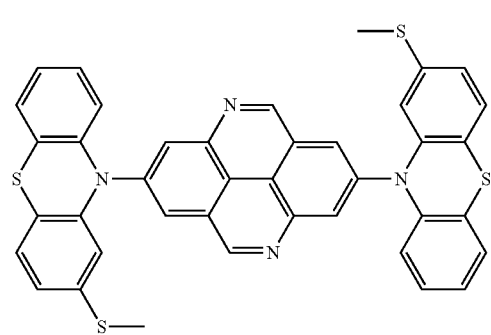
P48 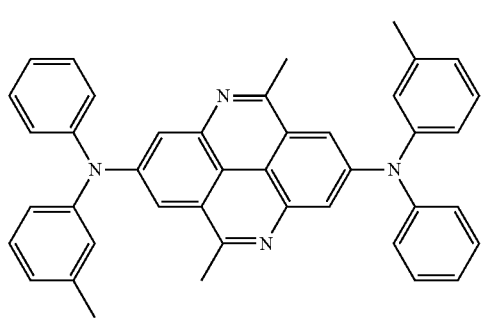
P49 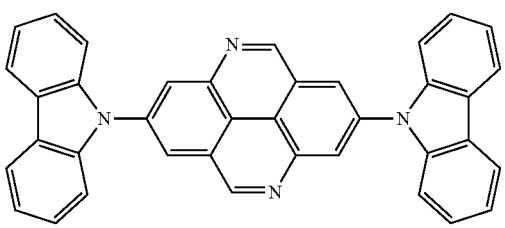
P50 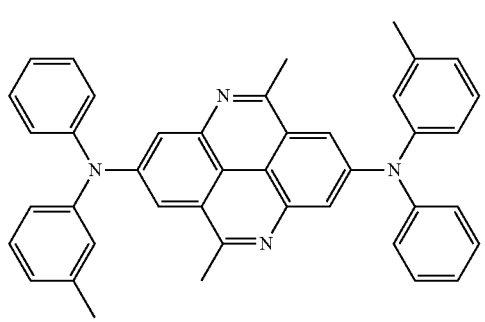
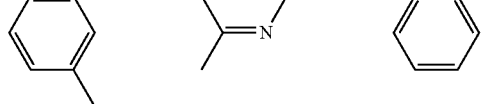
P51 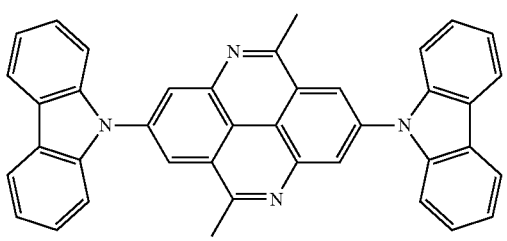
P52 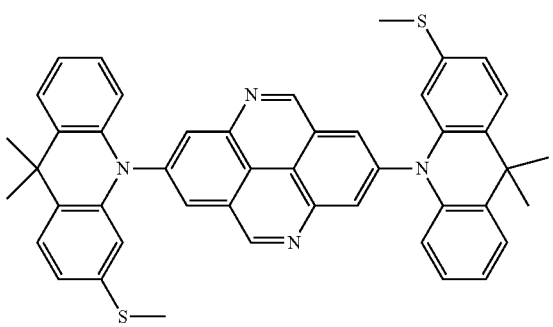
P53 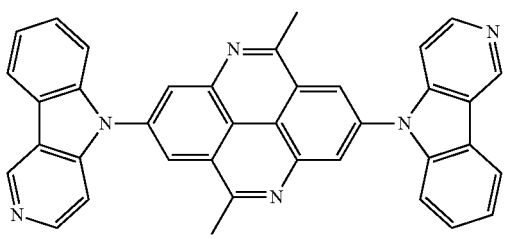
P54 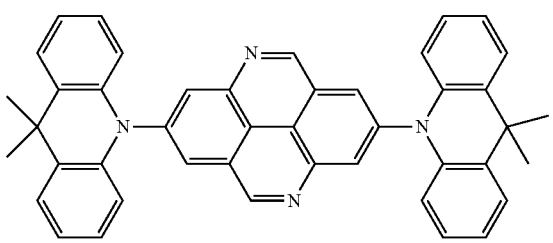
P55 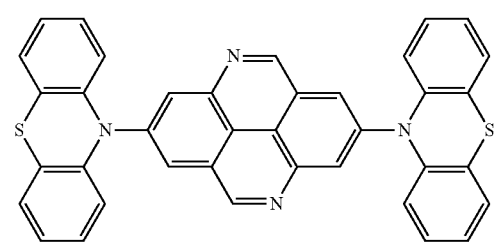
P56 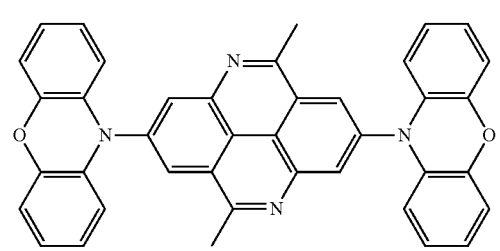

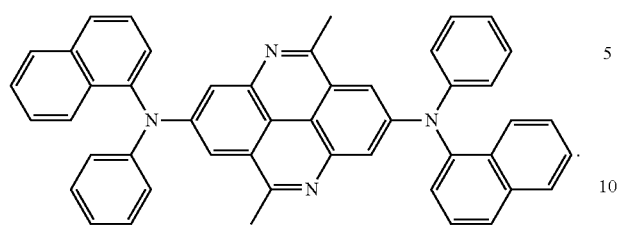
P57
17. The compound according to claim 1, wherein the compound is selected from any one of
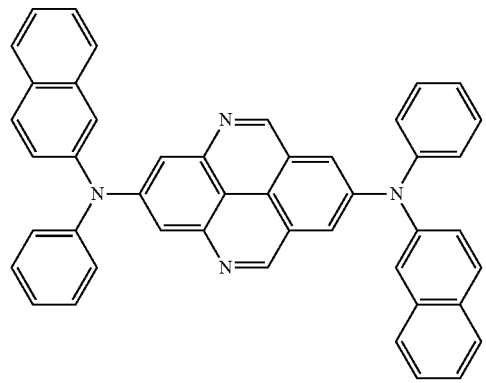
P28
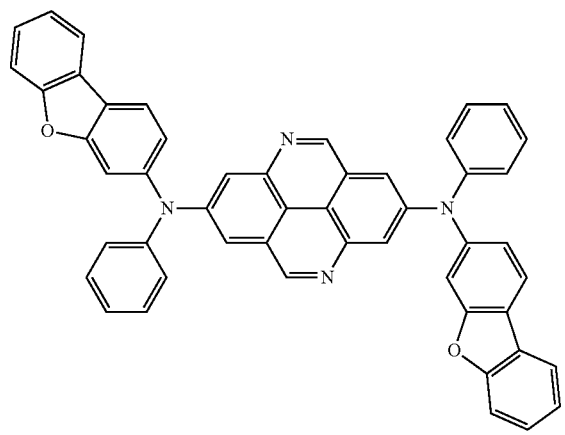
P1
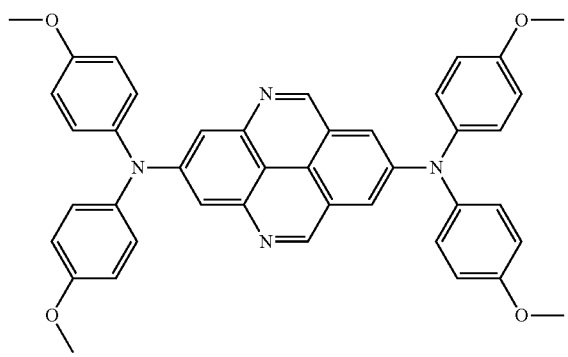
P30
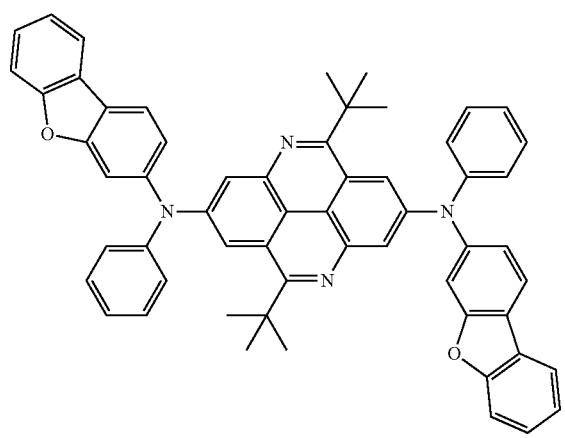
P5
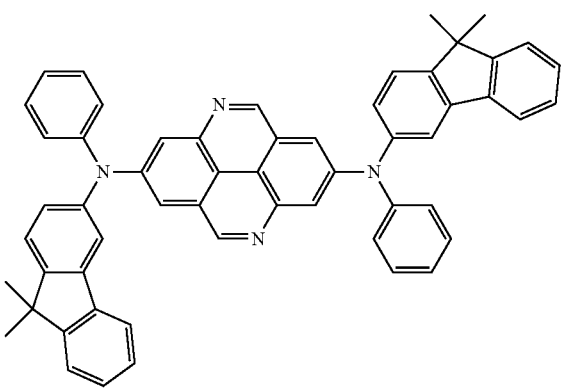
P45
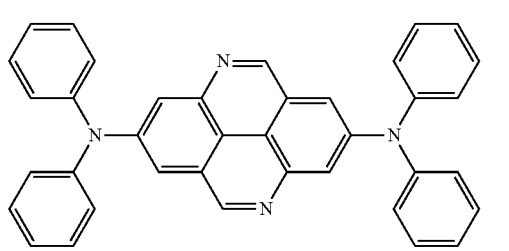
P25
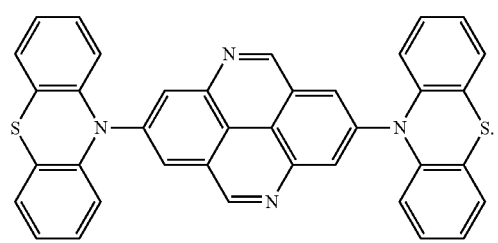
P49
P55

18. An OLED display panel, wherein the OLED display panel comprises a first electrode, a second electrode and an organic film layer arranged between the first electrode and the second electrode;

the organic film layer comprises a luminescent layer; and a luminescent material of the luminescent layer comprises the compound according to claim 1.

19. The OLED display panel according to claim 18, wherein the luminescent material serves as a host material or a guest material of the luminescent layer, or the luminescent material independently forms the luminescent layer to prepare a non-doped OLED display panel.

20. A display device, wherein the display device comprises the OLED display panel according to claim 18.

* * * * *